(12) United States Patent
Bobula et al.

(10) Patent No.: US 10,414,832 B2
(45) Date of Patent: Sep. 17, 2019

(54) DERIVATIVES OF SULFATED POLYSACCHARIDES, METHOD OF PREPARATION, MODIFICATION AND USE THEREOF

(71) Applicant: Contipro a.s., Dolni Dobrouc (CZ)

(72) Inventors: Tomas Bobula, Svit (SK); Radovan Buffa, Humenne (SK); Hana Vagnerova, Dolni Cermna (CZ); Romana Sulakova, Usti nad Orlici (CZ); Lucie Wolfova, Opava (CZ); Lenka Kohutova, Frydlant nad Ostravici (CZ); Veronika Moravcova, Letohrad (CZ); Ondrej Zidek, Litomysl (CZ); Pavlina Prochazkova, Vlkos (CZ); Vladimir Velebny, Zamberk (CZ)

(73) Assignee: Contipro a.s, Dolni Dobrouc, Czechia ( * ) Notice: Subject to any disclaimer, the term of this patent is extended or adjusted under 35 U.S.C. 154(b) by 0 days.

(21) Appl. No.: 15/737,443

(22) PCT Filed: Jun. 24, 2016

(86) PCT No.: PCT/CZ2016/000071
§ 371 (c)(1),
(2) Date: Dec. 18, 2017

(87) PCT Pub. No.: WO2016/206661
PCT Pub. Date: Dec. 29, 2016

(65) Prior Publication Data
US 2018/0171034 A1 Jun. 21, 2018

(30) Foreign Application Priority Data
Jun. 26, 2015 (CZ) .............................. PV2015-445

(51) Int. Cl.
*C08B 37/00* (2006.01)
*C08G 81/00* (2006.01)
(Continued)

(52) U.S. Cl.
CPC ........ *C08B 37/0069* (2013.01); *A61K 31/198* (2013.01); *A61K 38/06* (2013.01);
(Continued)

(58) Field of Classification Search
CPC . C08B 37/0069; C08B 37/0042; A61K 47/61; A61K 47/36; C08J 3/24; C08G 81/00; A61L 27/52
See application file for complete search history.

(56) References Cited

U.S. PATENT DOCUMENTS 3,075,527 A 1/1963 Bechtold
3,720,662 A 3/1973 Tessler et al.
(Continued)

FOREIGN PATENT DOCUMENTS

CA 2512730 A1 7/2004
CH 628088 A5 2/1982
(Continued)

OTHER PUBLICATIONS

International Search Report in International Patent Application No. PCT/CZ2010/000030, dated Sep. 1, 2010, 3 pgs.
(Continued)

Primary Examiner — Jonathan S Lau
(74) Attorney, Agent, or Firm — Wood Herron & Evans LLP

(57) ABSTRACT

The invention relates to the preparation and the use of $\alpha,\beta$-unsaturated aldehydes in the structure of sulfated polysaccharides. It concerns the derivatives with a conjugated double bond in the 4th and 5th positions of the galactopyranose part situated in the 6th position with respect to the aldehyde, according to the general structural formula (I) or its hydrated form according to the general structural formula (II). The preparation of these derivatives derives from sulfated polysaccharides containing a galactopyranose ring sulfated in the 4th position that is bound in the polymer chain via $\alpha(1\rightarrow3)$ or $\beta(1\rightarrow3)$ O-glycosidic bond. In the described solution, the sulfated polysaccharides undergo a regio- and chemoselective oxidation to form C6-saturated aldehyde, which, via a direct elimination of the sulfate group, provides the $\alpha,\beta$-unsaturated derivative according to the general formula (I) or (II). The described solution is technically advantageous, because it leads directly to $\alpha,\beta$-unsaturated aldehydes, without any elimination agents, higher temperature, or isolation of intermediates during the synthesis. The conjugation in the structure of $\alpha,\beta$-unsaturated aldehyde allows, under physiological conditions, to bind a wide variety of biocompatible amines in the structure of the sulfated polysaccharides. The proposed method allows to prepare materials suitable for pH-responsive drug delivery systems, or for the preparation of scaffolds in tissue engineering or regenerative medicine. Formulae for the abstract (I), (II) above, where R is OH, O—SO$_2$—OH, O—SO$_2$—ONa, or NH—Ac.

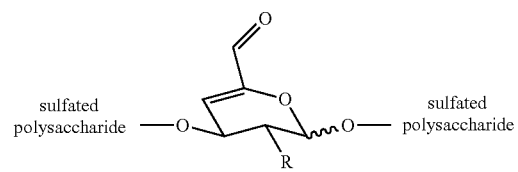

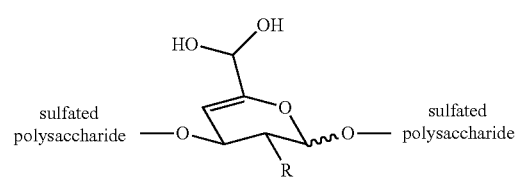

19 Claims, 2 Drawing Sheets

(51) Int. Cl.

| | | |
|---|---|---|
| *C08J 3/24* | (2006.01) | |
| *A61K 47/61* | (2017.01) | |
| *A61K 47/36* | (2006.01) | |
| *A61L 27/20* | (2006.01) | |
| *A61L 27/52* | (2006.01) | |
| *A61K 31/198* | (2006.01) | |
| *A61K 38/06* | (2006.01) | |
| *C08B 37/08* | (2006.01) | |

(52) U.S. Cl.
CPC .............. *A61K 47/36* (2013.01); *A61K 47/61* (2017.08); *A61L 27/20* (2013.01); *A61L 27/52* (2013.01); *C08B 37/0042* (2013.01); *C08B 37/0072* (2013.01); *C08G 81/00* (2013.01); *C08J 3/24* (2013.01); *C08J 2305/00* (2013.01); *C08J 2305/08* (2013.01)

(56) References Cited

U.S. PATENT DOCUMENTS

| | | |
|---|---|---|
| 3,728,223 A | 4/1973 | Kaneko et al. |
| 4,043,331 A | 8/1977 | Martin et al. |
| 4,205,025 A | 5/1980 | Hart et al. |
| 4,258,134 A | 3/1981 | Yoshida et al. |
| 4,713,448 A | 12/1987 | Balazs et al. |
| 4,761,401 A | 8/1988 | Couchman et al. |
| 4,851,521 A | 7/1989 | Della Valle et al. |
| 4,965,353 A | 10/1990 | Della Valle et al. |
| 5,455,349 A | 10/1995 | Grasshoff et al. |
| 5,462,976 A | 10/1995 | Matsuda et al. |
| 5,520,916 A | 5/1996 | Dorigatti et al. |
| 5,522,879 A | 6/1996 | Scopelianos |
| 5,550,225 A | 8/1996 | Philippe |
| 5,616,568 A | 4/1997 | Pouyani et al. |
| 5,658,582 A | 8/1997 | Dorigatti et al. |
| 5,676,964 A | 10/1997 | Della Valle et al. |
| 5,690,961 A | 11/1997 | Nguyen |
| 5,824,335 A | 10/1998 | Dorigatti et al. |
| 5,868,973 A | 2/1999 | Muller et al. |
| 6,025,444 A | 2/2000 | Waki et al. |
| 6,075,066 A | 6/2000 | Matsuda et al. |
| 6,162,537 A | 12/2000 | Martin et al. |
| 6,207,134 B1 | 3/2001 | Fahlvik et al. |
| 6,288,043 B1 | 9/2001 | Spiro et al. |
| 6,509,039 B1 | 1/2003 | Nies |
| 6,613,897 B1 | 9/2003 | Yatsuka et al. |
| 6,632,802 B2 | 10/2003 | Bellini et al. |
| 6,641,798 B2 | 11/2003 | Achilefu et al. |
| 6,673,919 B2 | 1/2004 | Yui et al. |
| 6,683,064 B2 | 1/2004 | Thompson et al. |
| 6,719,986 B1 | 4/2004 | Wohlrab et al. |
| 6,902,548 B1 | 6/2005 | Schuler et al. |
| 6,953,784 B2 | 10/2005 | Thompson et al. |
| 7,125,860 B1 | 10/2006 | Renier et al. |
| 7,214,759 B2 | 5/2007 | Pacetti et al. |
| 7,345,117 B1 | 3/2008 | Barbucci et al. |
| 7,550,136 B2 | 6/2009 | Warner et al. |
| 7,680,038 B1 | 3/2010 | Gourlay |
| 7,951,936 B2 | 5/2011 | Sato |
| 8,062,654 B2 | 11/2011 | Nelson et al. |
| 8,129,449 B2 | 3/2012 | Heinzman et al. |
| 8,143,391 B2 | 3/2012 | Yasugi et al. |
| 8,247,546 B2 | 8/2012 | Stucchi et al. |
| 9,017,725 B2 | 4/2015 | Mitra et al. |
| 9,492,586 B2 | 11/2016 | Wolfova et al. |
| 9,522,966 B2 | 12/2016 | Buffa et al. |
| 2002/0016472 A1 | 2/2002 | Tsien et al. |
| 2002/0026039 A1 | 2/2002 | Bellini et al. |
| 2002/0076810 A1 | 6/2002 | Radice et al. |
| 2003/0113354 A1 | 6/2003 | Schmid et al. |
| 2003/0163073 A1 | 8/2003 | Effing et al. |
| 2003/0205839 A1 | 11/2003 | Bachrach |
| 2004/0101546 A1 | 5/2004 | Gorman et al. |
| 2004/0192643 A1 | 9/2004 | Pressato et al. |
| 2005/0112349 A1 | 5/2005 | Laurencin et al. |
| 2005/0118231 A1 | 6/2005 | El Meski et al. |
| 2005/0119219 A1 | 6/2005 | Bellini et al. |
| 2005/0126338 A1 | 6/2005 | Yadav |
| 2005/0266546 A1 | 12/2005 | Warner et al. |
| 2006/0046590 A1 | 3/2006 | Chu et al. |
| 2006/0084759 A1 | 4/2006 | Calabro et al. |
| 2006/0188578 A1 | 8/2006 | Fernandez et al. |
| 2006/0189516 A1 | 8/2006 | Yang et al. |
| 2006/0216324 A1 | 9/2006 | Stucke et al. |
| 2006/0281912 A1 | 12/2006 | James et al. |
| 2007/0149441 A1 | 6/2007 | Aeschlimann et al. |
| 2007/0202084 A1 | 8/2007 | Sadozai et al. |
| 2008/0009630 A1 | 1/2008 | Gao et al. |
| 2008/0063617 A1 | 3/2008 | Abrahams et al. |
| 2008/0071001 A1 | 3/2008 | Sato |
| 2008/0124395 A1 | 5/2008 | Chen et al. |
| 2008/0286300 A1 | 11/2008 | Bardotti et al. |
| 2009/0024019 A1 | 1/2009 | Stein et al. |
| 2009/0028788 A1 | 1/2009 | Achilefu |
| 2009/0180966 A1 | 7/2009 | Borbely et al. |
| 2009/0252810 A1 | 10/2009 | Tommeraas et al. |
| 2010/0002155 A1 | 1/2010 | Yamaguchi et al. |
| 2010/0172892 A1 | 7/2010 | Uvarkina et al. |
| 2010/0207078 A1 | 8/2010 | Marder et al. |
| 2010/0247908 A1 | 9/2010 | Velev et al. |
| 2010/0310631 A1 | 12/2010 | Domard et al. |
| 2010/0310853 A1 | 12/2010 | Schwiegk et al. |
| 2010/0316682 A1 | 12/2010 | Chen et al. |
| 2011/0020917 A1 | 1/2011 | Wen et al. |
| 2011/0028062 A1 | 2/2011 | Chester et al. |
| 2011/0104070 A1 | 5/2011 | Kang et al. |
| 2011/0111012 A1 | 5/2011 | Pepper et al. |
| 2011/0196328 A1 | 8/2011 | Bellini et al. |
| 2011/0200676 A1 | 8/2011 | Lin et al. |
| 2011/0218331 A1 | 9/2011 | Buffa et al. |
| 2011/0229551 A1 | 9/2011 | Doshi et al. |
| 2011/0263724 A1 | 10/2011 | Gurtner et al. |
| 2012/0040463 A1 | 2/2012 | Domard et al. |
| 2012/0095205 A1 | 4/2012 | Buffa et al. |
| 2012/0245323 A1 | 9/2012 | Buffa et al. |
| 2012/0264913 A1 | 10/2012 | Buffa et al. |
| 2012/0277416 A1 | 11/2012 | Carter et al. |
| 2012/0289478 A1 | 11/2012 | Rovati |
| 2013/0017367 A1 | 1/2013 | Ravagnan et al. |
| 2013/0136784 A1 | 5/2013 | Staab |
| 2013/0195791 A1 | 8/2013 | Berkland et al. |
| 2013/0309706 A1 | 11/2013 | Kruglick |
| 2014/0120069 A1 | 5/2014 | Huerta-Angeles et al. |
| 2014/0242145 A1 | 8/2014 | Yoo et al. |
| 2015/0157463 A1 | 6/2015 | Stad et al. |
| 2015/0320873 A1 | 11/2015 | Smejkalova et al. |

FOREIGN PATENT DOCUMENTS

| | | |
|---|---|---|
| CN | 101897976 A | 12/2010 |
| CN | 102154738 A | 8/2011 |
| CN | 103505736 A | 1/2014 |
| CN | 103789874 A | 5/2014 |
| CZ | 2006605 A3 | 4/2008 |
| CZ | 20070299 A3 | 2/2009 |
| CZ | 301899 B6 | 7/2010 |
| CZ | 302503 B6 | 6/2011 |
| CZ | 302504 B6 | 6/2011 |
| CZ | 302856 B6 | 12/2011 |
| CZ | 302994 B6 | 2/2012 |
| CZ | 20101001 A3 | 2/2012 |
| CZ | 303879 B6 | 6/2013 |
| CZ | 304072 B6 | 9/2013 |
| CZ | 304266 B6 | 2/2014 |
| CZ | 304303 B6 | 2/2014 |
| CZ | 20120537 A3 | 3/2014 |
| CZ | 304512 B6 | 6/2014 |
| CZ | 305153 B6 | 5/2015 |
| DE | 10331342 A1 | 2/2005 |
| EP | 0161887 A2 | 11/1985 |
| EP | 0216453 A2 | 4/1987 |
| EP | 0763754 A2 | 3/1997 |
| EP | 0554898 B1 | 5/1997 |

(56) References Cited

FOREIGN PATENT DOCUMENTS

| | | |
|---|---|---|
| EP | 1369441 A1 | 12/2003 |
| EP | 1454913 A1 | 9/2004 |
| EP | 1115433 B1 | 12/2004 |
| EP | 1538166 A1 | 6/2005 |
| EP | 1217008 B1 | 3/2006 |
| EP | 1826274 A1 | 8/2007 |
| EP | 1905456 A1 | 4/2008 |
| EP | 1607405 B1 | 5/2011 |
| EP | 2399940 A2 | 12/2011 |
| EP | 2522337 A2 | 11/2012 |
| EP | 2899214 A1 | 7/2015 |
| JP | 62104579 A | 5/1987 |
| JP | 63044883 A | 11/1988 |
| JP | H0214019 A | 1/1990 |
| JP | H0347801 A | 2/1991 |
| JP | 06025306 A | 2/1994 |
| JP | H0625306 A | 2/1994 |
| JP | 3308742 B2 | 7/2002 |
| JP | 2004507586 A | 3/2004 |
| JP | 2004123785 A | 4/2004 |
| JP | 2007262595 A | 10/2007 |
| JP | 3975267 B2 | 12/2007 |
| JP | 2008208480 A | 9/2008 |
| JP | 2008295885 A | 12/2008 |
| JP | 2010138276 A | 6/2010 |
| KR | 20070118730 A | 12/2007 |
| KR | 20080062092 A | 7/2008 |
| KR | 20080111815 A | 12/2008 |
| KR | 20120118681 A | 10/2012 |
| KR | 20130085294 A | 7/2013 |
| NL | 9700003 A | 7/1997 |
| WO | 199311803 A1 | 6/1993 |
| WO | 199627615 A1 | 9/1996 |
| WO | 9637519 A1 | 11/1996 |
| WO | 1996035720 A1 | 11/1996 |
| WO | 199808876 A1 | 3/1998 |
| WO | 199901143 A1 | 1/1999 |
| WO | 199957158 A1 | 11/1999 |
| WO | 0063470 A1 | 10/2000 |
| WO | 0134657 A1 | 5/2001 |
| WO | 0218448 A2 | 3/2002 |
| WO | 0218450 A1 | 3/2002 |
| WO | 0232913 A1 | 4/2002 |
| WO | 2002032285 A2 | 4/2002 |
| WO | 0248197 A1 | 6/2002 |
| WO | 02057210 A1 | 7/2002 |
| WO | 2004061171 A2 | 7/2004 |
| WO | 2005028632 A2 | 3/2005 |
| WO | 2005092390 A2 | 10/2005 |
| WO | 2005092929 A1 | 10/2005 |
| WO | 2006010066 A2 | 1/2006 |
| WO | 2006026104 A2 | 3/2006 |
| WO | 2006056204 A1 | 6/2006 |
| WO | 2006102374 A2 | 9/2006 |
| WO | 2007003905 A1 | 1/2007 |
| WO | 2007006403 A2 | 1/2007 |
| WO | 2007009728 A2 | 1/2007 |
| WO | 2007033677 A1 | 3/2007 |
| WO | 2007101243 A1 | 9/2007 |
| WO | 2008014787 A1 | 2/2008 |
| WO | 2008031525 A1 | 3/2008 |
| WO | 2008077172 A2 | 7/2008 |
| WO | 2008115799 A1 | 9/2008 |
| WO | 2009037566 A2 | 3/2009 |
| WO | 2009050389 A2 | 4/2009 |
| WO | 2009108100 A1 | 9/2009 |
| WO | 2009148405 A1 | 12/2009 |
| WO | 2010018324 A1 | 2/2010 |
| WO | 2010028025 A1 | 3/2010 |
| WO | 2010051783 A1 | 5/2010 |
| WO | 2010061005 A1 | 6/2010 |
| WO | 2010095049 A1 | 8/2010 |
| WO | 2010095052 A2 | 8/2010 |
| WO | 2010095056 A2 | 8/2010 |
| WO | 2010105582 A1 | 9/2010 |
| WO | 2010130810 A1 | 11/2010 |
| WO | 2010138074 A1 | 12/2010 |
| WO | 2011014432 A1 | 2/2011 |
| WO | 2011028031 A2 | 3/2011 |
| WO | 2011059325 A2 | 5/2011 |
| WO | 2011059326 A2 | 5/2011 |
| WO | 2011069474 A2 | 6/2011 |
| WO | 2011069475 A2 | 6/2011 |
| WO | 2012034544 A2 | 3/2012 |
| WO | 2012089179 A1 | 7/2012 |
| WO | 2012146218 A1 | 11/2012 |
| WO | 2013056312 A1 | 4/2013 |
| WO | 2013159757 A1 | 10/2013 |
| WO | 2013167098 A2 | 11/2013 |
| WO | 2013171764 A2 | 11/2013 |
| WO | 2014023272 A1 | 2/2014 |
| WO | 2014082608 A1 | 6/2014 |
| WO | 2014082609 A1 | 6/2014 |
| WO | 2014082611 A1 | 6/2014 |

OTHER PUBLICATIONS

International Search Report in International Patent Application No. PCT/CZ2010/000128, dated Jun. 9, 2011, 3 pgs.
International Search Report in International Patent Application No. PCT/CZ2010/000129, dated Jun. 15, 2011, 3 pgs.
International Search Report in International Patent Application No. PCT/CZ2011/000126, dated Apr. 12, 2012, 3 pgs.
International Search Report in International Patent Application No. PCT/CZ2012/000035, dated Aug. 28, 2012, 3 pgs.
International Search Report in International Patent Application No. PCT/CZ2013/000023, dated Aug. 9, 2013, 3 pgs.
International Search Report in International Patent Application No. PCT/CZ2013/000057, dated Jul. 24, 2013, 4 pgs.
International Search Report in International Patent Application No. PCT/CZ2013/000063, dated Apr. 23, 2015, 7 pgs.
International Search Report in International Patent Application No. PCT/CZ2013/000091, dated Oct. 31, 2013, 3 pgs.
International Search Report in International Patent Application No. PCT/CZ2013/000116, dated Jan. 28, 2014, 4 pgs.
International Search Report in International Patent Application No. PCT/CZ2013/000155, dated Feb. 19, 2014, 4 pgs.
International Search Report in International Patent Application No. PCT/CZ2013/000156, dated Apr. 4, 2014, 5 pgs.
International Search Report in International Patent Application No. PCT/CZ2013/000157, dated Mar. 19, 2014, 3 pgs.
International Search Report in International Patent Application No. PCT/CZ2013/000158, dated Mar. 19, 2014, 3 pgs.
International Search Report in International Patent Application No. PCT/CZ2014/000138, dated May 4, 2015, 4 pgs.
International Search Report in International Patent Application No. PCT/CZ2015/000018, dated Jul. 22, 2015, 5 pgs.
International Search Report in International Patent Application No. PCT/CZ2015/000068, dated Jan. 8, 2016, 4 pgs.
International Search Report in International Patent Application No. PCT/CZ2016/000027, dated Jun. 27, 2016, 3 pgs.
International Search Report in International Patent Application No. PCT/CZ2016/000065, dated Sep. 30, 2016, 5 pgs.
International Search Report in International Patent Application No. PCT/CZ2016/050036, dated Feb. 6, 2017, 4 pgs.
International Search Report in International Patent Application No. PCT/CZ2016/050048, dated May 3, 2017, 4 pgs.
International Search Report in International Patent Application No. PCT/EP2016/064653, dated Aug. 25, 2016, 4 pgs.
Jacoboni, I., "Hyaluronic Acid by Atomic Force Microscopy," Journal of Structural Biology vol. 126, 1999, pp. 52-58.
Jahn, M. et al., "The reaction of hyaluronic acid and its monomers glucuronic acid and N-acetylglucosamine, with reactive oxygen species," Carbohydrate Research, 1999, vol. 321, pp. 228-234.
Japanese Official Action (English language translation) in Japanese Patent Application No. 2012-542355, dated Oct. 17, 2014.
Japanese Official Action (English language translation) in Japanese Patent Application No. 2014-506754, dated Jan. 22, 2015, 2 pgs.

(56) References Cited

OTHER PUBLICATIONS

Japanese Official Action (including English language translation) in Japanese Patent Application No. 2012-542356, dated Oct. 3, 2014, 8 pgs.
Japanese Official Action in Japanese Patent Application No. 2015-543316, 5 pgs.
Ji, Y. et al., "Electrospun three-dimensional hyaluronic acid nanofibrous scaffolds," Biomaterials (2006)27(1):3782-3792.
Jia, X.Q. et al., "Synthesis and Characterization of in Situ Cross-Linkable Hyaluronic Acid-Based Hydrogels with Potential Application for Vocal Fold Regeneration," Macromolecules (2004) 37:3239-3248.
Jiang, B. et al., "Study on TEMPO-mediated selective oxidation of hyaluronan and the effects of salt on the reaction kinetics," Carbohydrate Research, Pergamon, GB (2000) 327(4)455-461.
Jin, R. et al., "Enzyme-mediated fast in situ formation of hydrogels from dextran-tyramine conjugates," Biomaterials (2007) 28(18):2791-2800.
Job, D. et al., "Substituent effect on the oxidation of phenols and aromatic amines by horseradish peroxidase compound I," Eur J Biochem 1976, 66 (3), 607-14.
Jou, Chi-Hsiung et al., "Biocompatibility and Antibacterial Activity of Chitosan and Hyaluronic Acid Immobilized Polyester Fibers," Journal of Applied Polymer Science vol. 104, No. 1, 2007, pp. 220-225.
Juhlin, L., "Hyaluronan in skin," Journal of Internal Medicine (1997) 242:61-66.
Kalyanaraman, B. et al., "Peroxidatic oxidation of catecholamines. A kinetic electron spin resonance investigation using the spin stabilization approach" Journal of Biological Chemistry (1984) 259(12)7584-7589.
Katritzky, A.R. et al., "Cycloaddition Reactions of Heteroaromatic Six-Membered Rings," Chem. Rev. (1989)89:827-861.
Katz, S.A. et al., "The Toxicology of Chromium with Respect to its Chemical Speciation: a Review," Journal of Applied Toxicology (1993) 13(3):217-224.
Kawaguchi, Y. et al., "The relation between the adsorption behavior at the interface and the conformational changes in hyaluronates partially modified with various acyl chains," Carbohydrate Polymers (1995) 26:149-154.
Kedar, U. et al., "Advances in polymeric micelles for drug delivery and tumor targeting," Nanomedicine: Nanotechnology, Biology, and Medicine (2010) 6(6):714-729.
Khetan, S. et al., "Patterning network structure to spatially control cellular remodeling and stem cell fate within 3-dimensional hydrogels," Biomaterials (2010) 31(32):8228-8234.
Kim, B. et al., "Complexation Phenomena in pH-Responsive Copolymer Networks with Pendent Saccarides," Macromol. (2002) 35:9545-9550.
Kim, T.G. et al., "Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel," Biomacromolecules (2009) 10(6):1532-1539.
Klan, P. et al., "Photoremovable Protecting Groups in Chemistry and Biology: Reaction Mechanisms and Efficacy," Chem. Rev. (2013) 113(1):119-191.
Korsmeyer, R.W. et al., "Mechanisms of solute release from porous hydrophilic polymers," International Journal of Pharmaceutics (1983) 15:25-35.
Kumar, A. et al., "Development of hyaluronic acid-Fe2O3 hybrid magnetic nanoparticles for targeted delivery of peptides," Nanomedicine: Nanotechnology, Biology and Medicine, Elsevier, NL (2007) 3(2)132-137.
Kuo, J.W., "Practical Aspects of Hyaluronan Based Medical Products," 2006, CRC Press, Taylor & Francis Group, pp. 60-61.
Lapcik, L. Jr. et al., Chemicke Listy vol. 85, 1991, pp. 281-298.
Laurent, S. et al., "Magnetic fluid hyperthennia: Focus on superparamagnetic iron oxide nanoparticles," Advances in Colloid and Interface Science (2011) 166:8-23.

Leach, J.B. et al., "Characterization of protein release from photocrosslinkable hyaluronic acid-polyethylene glycol hydrogel tissue engineering scaffolds," Biomaterials (2005) 26:125-135.
Leach, J.B. et al., "Photocrosslinked Hyaluronic Acid Hydrogels: Natural, Biodegradable Tissue Engineering Scaffolds," Biotechnol Bioeng. (2003) 82:578-589.
Lee, Dong-Eun et al., "Amphiphilic hyaluronic acid-based nanoparticles for tumor-specific optical/MR dual imaging," Journal of Materials Chemistry (2012) 22(1):10444-10447.
Lee, F. et al., "An injectable enzymatically crosslinked hyaluronic acid-tyramine hydrogel system with independent tuning of mechanical strength and gelation rate," Soft Matter (2008) 4:880-887.
Lee, F. et al., "An injectable hyaluronic acid-tyramine hydrogel system for protein delivery," Journal of Controlled Release (2009) 134:186-193.
Lee, K.Y. et al., "Electrospinning of polysaccharides for regenerative medicine," Advanced Drug Delivery Reviews (2009) 61:1020-1032.
Lee, S.A. et al., "Spectroscopic studies of the physical properties of hyaluronate films: the origin of the phase transition," Carbohydrate Polymers (1995) 28:61-67.
Lee, Yuhan et al., "Bioinspired Surface Immobilization of Hyaluronic Acid on Monodisperse Magnetite Nanocrystals for Targeted Cancer Imaging," Advanced Materials (2008) 20:4154-4157.
Li, J. et al., "Electrospinning of Hyaluronic Acid (HA) and HA/Gelatin Blends," Macromolecular Rapid Communications (2006) 27:114-120.
Li, J. et al., "Redox-sensitive micelles self-assembled from amphiphilic hyaluronic acid-deoxycholic acid conjugates for targeted intracellular delivery of paclitaxel," Biomaterials (2012) 33(7):2310-2320.
Li, M. et al., Comparison of Two Ultrasmall Superparamagnetic Iron Oxides on Cytotoxicity and MR Imaging of Tumors, Theranostics (2012) 2(1):76-85.
Liang, Y. et al., "An in situ formed biodegradable hydrogel for reconstruction of the corneal endothelium," Colloids and Surfaces B: Biointerfaces (2011) 82(1):1-7.
Linhardt, R.J. et al., "Polysaccharide lyases," Applied Biochemistry and Biotechnology (1986) 12:135-176.
Linhartova, B., Nanovlakna na bazi hyaluronanu, Bakalarska prace, Vysoke uceni technicke v Brne, 2008 (English language Abstract on p. 3).
Liu, Yanchun et al., "Biocompatibility and stability of disulfide-crosslinked hyaluronan films," Biomaterials (2005) 26(23):4737-4746.
Liu, Yanhua et al., "Dual targeting folate-conjugated hyaluronic acid polymeric micelles for paclitaxel delivery," International Journal of Pharmaceutics (2011) 421(1):160-169.
Luo, S. et al., "A review of NIR dyes in cancer targeting and imaging," Biomaterials (2011) 32:7127-7138.
Luo, Yanfeng et al., "Novel amphoteric pH-sensitive hydrogels derived from ethylenediaminetetraacetic dianhydride, butanediamine and amino-terminated poly(ethylene glycol): Design, synthesis and swelling behavior," European Polymer Journal (2011) 47:40-47.
Maeda, H., "The Enhanced Permeability and Retention (EPR) Effect in Tumor Vasculature: The Key Role of Tumor-Selective Macromolecular Drug Targeting," Advances in Enzyme Regulation (2001) 41(1):189-207.
Malkoch, M. et al., "Synthesis of well-defined hydrogel networks using Click chemistry," Chem. Commun. (2006) 2774-2776.
Marega, R. et al., "Hyaluronan-Carbon Nanotube Derivatives: Synthesis, Conjugation with Model Drugs, and DOSY NMR Characterization," Eur. J. Org. Chem. (2011) 28:5617-5625.
Matsushima, R. et al., "Photoreactions of Alkylated 2-Pyridones," J. Chem. Soc. Perkin Trans. 2 (1985) 1445-1448.
Mayol, L. et al., "Amphiphilic hyaluronic acid derivatives toward the design of micelles for the sustained delivery of hydrophobic drugs," Carbohydrate Polymers (2014) 102:110-116.
Mazzone, S.B., "Fluorescent styryl dyes FM 1-43 and FM2-10 are muscarinic receptor antagonists: intravital visualization of receptor occupancy," The Journal of Physiology (2006) 575(1):23-35.
McIntyre, J.E., "The Chemistry of Fibres," Studies in Chemistry No. 6, 1971, p. 15.

(56) References Cited

OTHER PUBLICATIONS

McTaggart, L.E. et al., "Assessment of polysaccharide gels as drug delivery vehicles," Int. J. Pharm. 1993, vol. 100, pp. 199-206.
Merriam Webster Online Dictionary, obtained online at: http://www.merriam-webster.com/cgi-bin/dictionary?book=Dictionary&va=derivative, downloaded on Jul. 5, 2008.
Miki, K. et al., "Near-Infrard Dye-Conjugated Amphiphilic Hyaluronic Acid Derivatives as a Dual Contrast Agent for In Vivo Optical and Photoacoustic Tumor Imaging," Biomacromolecules (2015) 16:219-227.
Miller, R.J. et al., Chemistry and Biology of Hyaluronan : Medicinal Uses of Modified Hyaluronate. Elsevier Ltd. 2004. 505-528.
Nevell, T.P. et al., "Cellulose Chemistry and its Applications," 1985, John Wiley & Sons, pp. 455-479.
Normandin, L. et al., "Manganese Neurotoxicity: An Update of Pathophysiologic Mechanisms," Metab Brain Dis (2002) 17(4):375-387.
Office Action in U.S. Appl. No. 13/512,484, dated May 11, 2016, 8 pgs.
Office Action in U.S. Appl. No. 13/512,484, dated Oct. 1, 2015, 8 pgs.
Office Action in U.S. Appl. No. 13/512,484, dated Sep. 11, 2014, 8 pgs.
Office Action in U.S. Appl. No. 13/514,759, dated Jul. 30, 2015, 12 pgs.
Office Action in U.S. Appl. No. 13/514,759, dated Sep. 24, 2014, 10 pgs.
Office Action in U.S. Appl. No. 13/977,181, dated Jan. 22, 2016, 8 pgs.
Office Action in U.S. Appl. No. 14/113,527, dated Feb. 12, 2016, 11 pgs.
Office Action in U.S. Appl. No. 14/113,527, dated Sep. 8, 2016, 10 pgs.
Office Action in U.S. Appl. No. 14/395,575, dated Jul. 6, 2017, 9 pgs.
Office Action in U.S. Appl. No. 14/420,012, dated Jun. 16, 2016, 6 pgs.
Office Action in U.S. Appl. No. 14/430,731, dated May 19, 2016, 12 pgs.
Office Action in U.S. Appl. No. 14/647,185, dated Sep. 28, 2016, 5 pgs.
Office Action in U.S. Appl. No. 14/647,626, dated Feb. 17, 2017, 12 pgs.
Office Action in U.S. Appl. No. 14/647,626, dated Jul. 28, 2016, 35 pgs.
Office Action in U.S. Appl. No. 14/647,626, dated Jun. 16, 2017, 14 pgs.
Office Action in U.S. Appl. No. 14/647,626, dated Nov. 13, 2017, 18 pgs.
Office Action in U.S. Appl. No. 14/647,649, dated Apr. 19, 2018, 9 pgs.
Office Action in U.S. Appl. No. 14/647,649, dated Dec. 8, 2017, 9 pgs.
Office Action in U.S. Appl. No. 14/647,649, dated May 31, 2017, 11 pgs.
Office Action in U.S. Appl. No. 15/038,078, dated Mar. 1, 2018, 10 pgs.
De Figueiredo, R.M. et al., "N,N'-Carbonyldiimidazole-Mediated Cyclization of Amino Alcohols to Substituted Azetidines and Other N-Heterocycles," J. Org. Chem. (2006) 71(11):4147-4154.
Dilling, W.L. et al., "Organic Photochemistry. XII. the Photodimerization and Photoisomerization of 2-Pyridone and Its Monochloro Derivatives," Mol. Photochem. (1973) 5(4):371-409.
Ding, B. et al., "TEMPO-mediated selective oxidation of substituted polysaccharides—an efficient approach for the determination of the degree of substitution at C-6," Carbohydrate Research (2008) 343(18)3112-3116.
Donati, A. et al., "Solution Structure of Hyaluronic Acid Oligomers by Experimental and Theoretical NMR, and Molecular Dynamics Simulation," Biopolymers (2001) 59:434-445.

Dumitriu, S., "Characterization and Properties of Hyaluronic Acid (Hyaluronan)," by M. Milas et al., Chap. 22 of Polysaccharides: Structural Diversity and Functional Versatility, 1998, Marcel Dekker Inc., pp. 535-549.
Duncan, R. et al., "Nanomedicine(s) under the Microscope," Molecular Pharmaceutics (2011) 8(6):2101-2141.
Dunford, H.B. et al., "Kinetics of the oxidation of p-aminobenzoic acid catalyzed by horseradish peroxidase compounds I and II," J Biol Chem 1975, 250(8), 2920-32.
Eenschooten, C. et al "Preparation and structural characterisation of novel and versatile amphiphilic octenyl succinic anhydride-modified hyaluronic acid derivatives," Carbohydrate Polymers (2010) 79(3):597-605.
El-Dakdouki, M.H. et al., "Development of drug loaded nanoparticles for tumor targeting. Part 1: synthesis, characterization, and biological evaluation in 2D cell cultures," Nanoscale (2013) 5(9):3895-3903.
El-Dakdouki, M.H. et al., "Development of Multifunctional Hyaluronan-Coated Nanoparticles for Imaging and Drug Delivery to Cancer Cells," Biomacromolecules (2012) 13(4):1144-1151.
El-Sherbiny, I.M. et al., "Poly(ethylene glycol)-carboxymethyl chitosan-based pH-responsive hydrogels: photo-induced synthesis, characterization, swelling, and in vitro evaluation as potential drug carriers," Carbohydrate Research (2010) 345:2004-2012.
Elander, R.P., "Industrial production of β-lactam antibiotics," Applied Microbiology and Biotechnology (2003) 61:385-392.
European First Official Action in European Patent Application No. 10812840.6-1306, dated Jul. 2, 2013, 4 pgs.
European Second Official Action in European Patent Application No. 10812840.6-1306, dated Sep. 24, 2014, 5 pgs.
Feng, Qian et al., "Self-Assembly Behaviour of Hyaluronic Acid on Mica by Atomic Force Microscopy," vol. 20, No. 1, 2004, pp. 146-148 and 152 (English language Abstract p. 152).
Ferrero, C. et al., "Fronts movement as a useful tool for hydrophilic matrix release mechanism elucidation," International Journal of Pharmaceutics (2000) 202:21-28.
Ferruti, P. et al., "Novel Poly(amido-amine)-Based Hydrogels as Scaffolds for Tissue Engineering," Macromol. Biosci. (2005) 5:613-622.
Fleige, E. et al., "Stimuli-responsive polymeric nanocarriers for the controlled transport of active compounds: Concepts and applications," Advanced Drug Delivery Reviews (2012) 64(9):866-884.
Funakoshi, T. et al., "Novel chitosan-based hyaluronan hybrid polymer fibers as a scaffold in ligament tissue engineering," Journal of Biomedical Materials Reasearch, Part A (2005) 74A(3):338-346.
Furuta, T. et al., "Anthraquinon-2-ylmethoxycarbonyl (Aqmoc): A New Photochemically Removable Protecting Group for Alcohols," Org. Lett. (2001) 3(12):1809-1812.
Ghan, R. et al., "Enzyme-Catalyzed Polymerization of Phenols within Polyelectrolyte Microcapsules," Macromolecules (2004) 37(12), 4519-4524.
Gibby, W.A., "Cross-Linked DTPA Polysaccharides for Magnetic Resonance Imaging, Synthesis and Relaxation Properties," Invest. Radiol. 1989, vol. 24, pp. 302-309.
Gilabert, M.A. et al., "Differential substrate behaviour of phenol and aniline derivatives during oxidation by horseradish peroxidase: kinetic evidence for a two-step mechanism," Biochim. Biophys. Acta. (2004) 1699:235-243.
Gilabert, M.A. et al., "Kinetic characterization of phenol and aniline derivates as substrates of peroxidase," Biol. Chem. (2004) 385(9):795-800.
Gilabert, M.A. et al., "Stereospecificity of horseradish peroxidase," Biol. Chem. (2004) 385:1177-1184.
Gobouri, A.A. et al., "Novel Synthesis of Diketo-Acid Chondroitin-4-sulfate as Coordination Biopolymer Precursor through Oxidation of Chondroitin-4-sulfate by Alkaline Permanganate," International Journal of Sciences (2013) 7:1-11.
Godula, K. et al., "Synthesis of Glycopolymers for Microarray Applications via Ligation of Reducing Sugars to a Poly (acryloyl hydrazide) Scaffold," J. Am. Chem. Soc. (2010) 132:9963-9965.
Gong, J. et al., "Polymeric micelles drug delivery system in oncology," Journal of Controlled Release (2012) 159 (3):312-323.

(56) References Cited

OTHER PUBLICATIONS

Green, T.W. et al., "Protective Groups in Organic Synthesis," 1999, New York: John Wiley & Sons, 3rd ed., Chap. 1, pp. 1-16.
Guillaumie, F. et al., "Comparative studies of various hyaluronic acids produced by microbial fermentation for potential topical ophthalmic applications," Journal of Biomedical Materials Research Part A (2009) 1421-1430.
Gupta, P. et al., "Hydrogels: from controlled release to pH-responsive drug delivery," Drug Discovery Today (2002) 7 (10):569-579.
Hasegawa, T. et al., "'Click chemistry' on polysaccharides: a convenient, general, and monitorable approach to develop (1-3)-β-D-glucans with various functional appendages," Carbohydrate Research (2006) 341:35-40.
Hassan, R. et al., "Kinetics and mechanism of oxidation of chondroitin-4-sulfate polysaccharide by chromic acid in aqueous perchlorate solutions," (2013) Carbohydrate Polymers 92:2321-6.
Hewson, W. D. et al., "Oxidation of P-cresol by horseradish peroxidase compound I," J Biol Chem 1976, 251 (19), 6036-6042.
Hewson, W. D. et al., "Stoichiometry of the reaction between horseradish peroxidase and p-cresol," J Biol Chem 1976, 251(19), 6043-52.
Higashimura, H. et al., Oxidative Polymerization. John Wiley & Sons, Inc. Olefin Fibers (2002) 10:740-764.
Hill, T. K. et al., "Indocyanine Green-Loaded Nanoparticles for Image-Guided Tumor Surgery," Bioconjugate Chem. (2015) 26:294-303.
Hocek, M., "Tvorba C-C A C-X Vazeb Cross-Coupling Reakcemi Katalyzovanymi Komplexy Prechodnych Kovu," Chem. Listy (2003) 97:1145-1150.
Hoffman, A.S., "'Intelligent' Polymers in Medicine and Biotechnology," Artificial Organs (1995) 19(5):458-467.
Hofmann, H. et al., "Conformational Changes of Hyaluronic Acid in Acid Medium," Albrecht Von Graefe's Archive for Clinical and Experimental Opthamology vol. 198, No. 1, 1976, pp. 95-100.
Holten, K.B. et al., "Appropriate Prescribing of Oral Beta-Lactam Antibiotics," American Family Physician (2000) 62 (3):611-620.
Huang, G. et al., "Superparamagnetic Iron Oxide Nanoparticles: Amplifying ROS Stress to Improve Anticancer Drug Efficacy.," Theranostics (2013) 3(2):116-126.
Huang, L. et al., "A Facsimile Method for Oxidation of Primary Alcohols to Caroxylic Acids and Its Application in Glycosaminoglycan Syntheses," Chemistry (2006) 12(20):5246-5252.
Huerta-Angeles, G. et al., "Synthesis of highly substituted amide hyaluronan derivatives with tailored degree of substitution and their crosslinking via click chemistry," Carbohydrate Polymers (2011) 84:1293-1300.
Huh, K.M. et al., "Hydrotropic polymer micelle system for delivery of paclitaxel," Journal of Controlled Release (2005) 101:59-68.
Hynes, W.L. et al., "Hyaluronidases of Gram-positive bacteria," FEMS Microbiology Letters (2000) 183:201-207.
Inanaga, J. et al., "A Rapid Esterification by Means of Mixed Anhydride and Its Application to Large-ring Lactonization," Bulletin of the Chemical Society of Japan (1979) 52(7):1989-1993.
International Preliminary Report on Patentability in International Patent Application No. PCT/CZ2010/000128, dated Feb. 5, 2013, 5 pgs.
International Preliminary Report on Patentability in International Patent Application No. PCT/CZ2010/000129, dated Jun. 12, 2012, 5 pgs.
International Search Report in International Patent Application No. PCT/CZ2009/000131, dated Apr. 9, 2010, 3 pgs.
Balan, V. et al., "Strategies to improve chitosan hemocompatibility: A review," European Polymer Journal (2004) 53:171-188.
Choi, W. II et al., Targeted antitumor efficacy and imaging via multifunctional nano-carrier conjugated with anti-HER2 trastuzumab, Nanomedicine: Nanotechnology, Biology, and Medicine (2015) 11:359-368.
Frangioni, J. V., "In vivo near-infrared fluorescence imaging," Curr. Opin. Chem. Biol. (2003) 7(5):626-634.
Funfstuck, V. V. et al., "Kontaktallergie gegenuber Dicyclohexylcarbodiimid," Dermatosen (1986) 34(4):110-111.
Huerta-Angeles, G. et al., "Novel synthetic method for the preparation of amphiphilic hyaluronan by means of aliphatic aromatic anhydrides," Carbohydrate Polymers (2014) 111:883-891.
Hussain, M. A. et al., "Acylation of Cellulose with N,N'-Carbonyldiimidazole-Activated Acids in the Novel Solvent Dimethyl Sulfoxide/Tetrabutylammonium Fluoride," Macromol. Rapid Commun. (2004) 25:916-920.
Kobayashi, H. et al., "New Strategies for Fluorescent Probe Design in Medical Diagnostic Imaging," Chem. Rev. (2010) 110(5):2620-2640.
Kokuryo, D. et al., "Corrigendum to SPIO-PICsome: Development of a highly sensitive and stealth-capable MRI nano-agent for tumor detection using SPIO-loaded unimellar polyion complex vesicles (PICsomes)," Journal of Controlled Release (2014) 178:125.
Lee, Dong-Eun et al., "Hyaluronidase-Sensitive SPIONs for MR/Optical Dual Imaging Nanoprobes," Marcomol. Res. (2011) 19(8):861-867.
Bobula, T. et al., "One-pot synthesis of alpha,beta-unsaturated polyaldehyde of chondroitin sulfate," Carbohydrate Polymers (2016) 136:1002-1009.
Bobula, T. et al., "Solid-state photocrosslinking of hyaluronan microfibres," Carbohydrate Polymers (2015) 125:153-160.
Brand-Williams, W. et al., "Use of a Free Radical Method to Evaluate Antioxidant Activity," LWT—Food Science and Technology (1995) 28:25-30.
Collins, M. N. et al., "Hyaluronic Acid Based Scaffolds for Tissue Engineering—A review," Carbohydrate Polymers (2013) 92:1262-1279.
Hacker, M. C. et al., "Multi-Functional Macromers for Hydrogel Design in Biomedical Engineering and Regenerative Medicine," Inter. J. of Mol. Sc. (2015) 16:27677-27706.
Horton, D. et al., "Synthesis of 2,3-Unsaturated Polysaccharides From Amylose and Xylan," Carbohydrate Research (1975) 40:345-352.
International Search Report in International Patent Application No. PCT/CZ2017/050026, dated Oct. 26, 2017, 2 pgs.
Kelly, S. J. et al., "Kinetic properties of *Streptococcus pneumoniae* hyaluronate lyase," Glycobiology (2001) 11 (4):297-304.
Khetan, S. et al., "Sequential crosslinking to control cellular spreading in 3-dimensional hydrogels," Soft Matter (2009) 5:1601-1606.
Kühn, A. V. et al., "Identification of hyaluronic acid oligosaccharides by direct coupling of capillary electrophoresis with electrospray ion trap mass spectrometry," Rapid Communications in Mass Spectrometry (2003) 17:576-582.
Mero, A. et al., "Hyaluronic Acid Bioconjugates for the Delivery of Bioactive Molecules," Polymers (2014) 6(2):346-369.
Nimmo, C. M. et al., "Diels-Alder Click Cross-Linked Hyaluronic Acid Hydrogels for Tissue Engineering," Biomacromolecules (2011) 12:824-830.
Vigo, T. L. et al., "Deoxycelluloses and Related Structures," Polymers for Advanced Technologies (1999) 10:311-320.
Written Opinion in International Patent Application No. PCT/CZ2017/050026, dated Oct. 26, 2017, 5 pgs.
Akkara, J.A. et al., "Synthesis and Characterization of Polymers Produced by Horseradish Peroxidase in Dioxane," Journal of Polymer Science Part A: Polymer Chemistry (1991) 29(11):1561-1574.
Aldrich, Chem Files Synthetic Methods Oxidation, May 2005, vol. 5, No. 1 pp. 1-11 (English language translation included).
Angelin, M. et al., "Direct, Mild, and Selective Synthesis of Unprotected Dialdo-Glycosides," European Journal of Organic Chemistry (2006):4323-4326.
Armstrong, D.C. et al., "Culture Conditions Affect the Molecular Weight Properties of Hyaluronic Acid Produced by *Streptococcus zooepidemicus*," Appl. Environ. Microbiol. (1997) 63(7):2759-2764.
Atkins, E.D.T. et al., "The Conformation of the Mucopolysaccharides," J. Biochem. (1972) 128:1255-1263.
Atkins, E.D.T. et al., "The Molecular Structure of Hyaluronic Acid," Biochemical Journal (1971) 125(4):92.
Aubry-Rozier, B., Revue Medicale Suisse (2012) 14:571.

(56) References Cited

OTHER PUBLICATIONS

Author unknown, "Readily Accessible 12-I-51 Oxidant for the Conversion of Primary and Secondary Alcohols to Aldehydes and Ketones," Journal of Organic Chemistry (1983) 84:4155-4156 (English language on pp. 2-3 of document).
Author unknown, Encyclopedia of Cellulose, Asakura Publishing Co., Ltd., Nov. 10, 2000, pp. 155-156 (English language translation included).
Baeurle, S.A. et al., "Effect of the counterion behavior on the frictional-compressive properties of chondroitin sulfate solutions," Polymer (2009) 50(7):1805-1813.
Baijal, K. P. et al., "Tumor-enhancing effects of cholic acid are exerted on the early stages of colon carcinogenesis via induction of aberrant crypt foci with an enhanced growth phenotype," Canadian Journal of Physiology and Pharmacology, 1998, 76(12), 1095-1102.
Bakke, M. et al., "Identification, characterization, and molecular cloning of a novel hyaluronidase, a member of glycosyl hydrolase family 16, from *Penicillium* spp.," FEBS Letters (2011) 585(1):115-120.
Banerji, S. et al., "Structures of the Cd44-hyaluronan complex provide insight into a fundamental carbohydrate-protein interaction," Nature structural and molecular biology (2007) 14:234-239.
Benedetti, L. et al., "Biocompatibility and biodegradation of different hyaluronan derivatives (Hyaff) implanted-in rats," Biomaterials (1993) 14(15):1154-1160.
Bezakova, Z. et al., "Effect of microwave irradiation on the molecular and structural properties of hyaluronan," Carbohydrate Polymers (2008) 73(4):640-646.
Bottegoni, C. et al., "Oral chondroprotection with nutraceuticals made of chondroitin sulphate plus glucosamine sulphate in osteoarthritis," Carb. Pol. (2014) 109:126-138.
Boyer, I.J., "Toxicity of dibutyltin, tributyltin and other organotin compounds to humans and to experimental animals," Toxicology (1989) 55(3), 253-298.
Breunig, M. et al., "Breaking up the correlation between efficacy and toxicity for nonviral gene delivery," PNAS (2007) 104(36):14454-14459.
Buffa, R. et al., "Branched hyaluronic acid, synthesis, analysis and biological properties," Journal of Tissue Engineenng and Regenerative Medicine (2014) 8(1):321.
Buffa, R. et al., "New method of immobilization of hyaluronic acid oligomers," Journal of Tissue Engineering and Regenerative Medicine (2014) 8(1):321-322.
Burdick, J.A. et al., "Controlled Degradation and Mechanical Behavior of Photopolymerized Hyaluronic Acid Networks," Biomacromolecules (2005) 6:386-391.
Burdick, J.A. et al., "Hyaluronic Acid Hydrogels for Biomedical Applications," Adv. Mater. (2011) 23:H41-H56.
Burke, J., Solubility Parameters: Theory and Application, The Book and Paper Group Annual, vol. Three, 1984, 62 pgs.
Burner, U. et al., "Transient-state and steady-state kinetics of the oxidation of aliphatic and aromatic thiols by horseradish peroxidase," FEBS Letters (1997) 411(2-3):269-274.
Carey, F.A. et al., Advanced Organic Chemistry Part A: Structure and Mechanisms, Plenum Press, New York and London, pp. 475-479 (1990).
Cayman Chemical, Stearic Acid, obtained online at: https://www.caymanchem.com/pdfs/10011298.pdf, p. 1. (Year: 2017).
Chen, H. et al., "A dual-targeting nanocamer based on modified chitosan micelles for tumor imaging and therapy," Polym. Chem. 2014, 5, 4734-4746.
Chen, L. et al., "Synthesis and pH sensitivity of carboxymethyl chitosan-based polyampholyte hydrogel for protein carrier matrices," Biomaterials (2004) 25:3725-3732.
Cherrick, G. R. et al., "Indocyanine Green: Observations on Its Physical Properties, Plasma Decay, and Hepatic Extraction," J.Clinical Investigation, 1960, 39, 592-600.
Choi, K. Y. et al., "Self-assembled hyaluronic acid nanoparticles as a potential drug carrier for cancer therapy: synthesis, characterization, and in vivo biodistribution," J. Mater. Chem. 2009, 19 (24), 4102-4107.
Choi, K. Y. et al., "Self-assembled hyaluronic acid nanoparticles for active tumor targeting," Biomaterials 2010, 31 (1), 106-114.
Chu et al., "Electro-Spinning and Electro-Blowing of Hyaluronic Acid," 2004, Biomacromolecules, vol. 5, pp. 1428-1436. (Year: 2004).
Contipro, Specialty Hyaluronan Chemicals Product Catalog, 52 pgs. (retrieved on Sep. 26, 2018). (Year: 2018).
Cornwell, M.J. et al., "A One-Step Synthesis of Cyclodextrin Monoaldehydes," Tetrahedron Letters (1995) 36 (46):8371-8374.
Crescenzi, V. et al., "Novel Hydrogels via Click Chemistry: Synthesis and Potential Biomedical Applications," Biomacromolecules (2007) 8:1844-1850.
Cumpstey, I., Review Article "Chemical Modification of Polysaccharides," ISRN Organic Chemistry (2013) Article ID 417672, 27 pgs.
Czech Official Action in Czech Patent Application No. PV 2008-705, dated Oct. 23, 2009, 2 pgs.
Czech Official Action in Czech Patent Application No. PV 2009-835, dated Aug. 2010, 2 pgs.
Czech Official Action in Czech Patent Application No. PV 2009-836, dated Aug. 6, 2010, 2 pages.
Czech Search Report in Czech Patent Application No. PV 2010-1001, dated Sep. 27, 2011, 1 pg.
Czech Search Report in Czech Patent Application No. PV 2011-241, dated Nov. 30, 2011, 1 pg.
Czech Search Report in Czech Patent Application No. PV 2012-136, dated Sep. 18, 2012, 3 pgs.
Czech Search Report in Czech Patent Application No. PV 2012-282, dated Jan. 30, 2013, 1 pg.
Czech Search Report in Czech Patent Application No. PV 2012-306, dated Feb. 11, 2013, 1 pg.
Czech Search Report in Czech Patent Application No. PV 2012-664, dated May 24, 2013, 3 pgs.
Czech Search Report in Czech Patent Application No. PV 2012-842, dated Aug. 19, 2013, 3 pgs.
Czech Search Report in Czech Patent Application No. PV 2012-843, dated Aug. 20, 2013, 1 pg.
D'Este, M. et al., "A systematic analysis of DMTMM vs EDC/NHS for ligation of amines to Hyaluronan in water," Carbohydr. Polym. 2014, 108, 239-246.
Darr, A. et al., "Synthesis and characterization of tyramine-based hyaluronan hydrogels," Journal of Materials Science: Materials in Medicine (2009) 20(1), 33-44.
Dawlee, S. et al., "Oxidized Chondroitin Sulfate-Cross-Linked Gelatin Matrixes: A New Class of Hydrogels," Biomacromolecules (2005) 6(4):2040-2048.
Office Action in U.S. Appl. No. 15/038,078, dated Nov. 3, 2017, 10 pgs.
Office Action in U.S. Appl. No. 15/038,078, dated Sep. 11, 2018, 9 pgs.
Office Action in U.S. Appl. No. 15/124,827, dated Dec. 7, 2017, 9 pgs.
Office Action in U.S. Appl. No. 15/322,776, dated Apr. 17, 2018, 27 pgs.
Office Action in U.S. Appl. No. 15/322,776, dated Jul. 14, 2017, 11 pgs.
Office Action in U.S. Appl. No. 15/322,776, dated Sep. 12, 2017, 23 pgs.
Office Action in U.S. Appl. No. 15/556,370, dated Aug. 2, 2018, 18 pgs.
Office Action in U.S. Appl. No. 15/737,894, dated Oct. 5, 2018, 27 pgs.
Oh, E.J. et al., "Target specific and long-acting delivery of protein, peptide, and nukleotide therapeutics using hyaluronic acid derivatives," J. Controlled Release vol. 141, 2010, pp. 2-12.
Pal, K. et al., "Biopolymers in Controlled-Release Delivery Systems," Modern Biopolymer Science (2009) 519-557.
Park, Y.D. et al., "Photopolymerized hyaluronic acid-based hydrogels and interpenetrating networks," Biomaterials (2003) 24:893-900.

(56) References Cited

OTHER PUBLICATIONS

Pasqui, D. et al., "Polysaccharide-Based Hydrogels: The Key Role of Water in Affecting Mechanical Properties," Polymers (2012) 4:1517-1534.
Patel, P.K. et al., "Kinetic studies on the oxidation of phenols by the horseradish peroxidase compound II," Biochim Biophys Acta (1997) 1339(1):79-87.
Perale, G. et al., "Hydrogels in Spinal Cord Injury Repair Strategies," ACS Chem. Neurosci. (2011) 2(7):336-345.
Piggot, A.M. et al., "Synthesis of a new hydrophilic O-nitrobenzyl photocleavable linker suitable for use in chemical proteomics," Tetr. Lett. (2005) 46(47):8241-8244.
Piluso, S. et al., "Hyaluronic acid-based hydrogels crosslinked by copper-catalyzed azide-alkyne cycloaddition with tailorable mechanical properties," International Journal of Artificial Organs (2011) 34:192-197, Abstract.
Prestwich, G.D., "Biomaterials from Chemically-Modified Hyaluronan," internet article, Feb. 26, 2001, 17 pgs.
Prestwich, G.D., "Hyaluronic acid-based clinical biomaterials derived for cell and molecule delivery in regenerative medicine," Journal of Controlled Release (2011) 155:193-199.
Price, Richard D. et al., "Hyaluronic acid: the scientific and clinical evidence," J. Plast. Reconstr. Aesthet. Surg. (2007) 60(10):1110-1119.
Qiu, Y. et al., "Environment-sensitive hydrogels for drug delivery," Advanced Drug Delivery Reviews (2001) 63:321-339.
Rao, K.V.R. et al., "Influence of Molecular Size and Water Solubility of the Solute on its Release from Swelling and Erosion Controlled Polymeric Matrices," Journal of Controlled Release (1990) 12:133-141.
Remy, H., Anorganicka chemie II., Sntl Praha 1971, pp. 306-321.
Ritger, P.L. et al., "A Simple Equation for Description of Solute Release I. Fickian and Non-Fickian Release from Non-Swellable Devices in the Form of Slabs, Spheres, Cylinders or Discs," Journal of Controlled Release (1987) 5:23-36.
Ritger, P.L. et al., "A Simple Equation for Description of Solute Release II. Fickian and Anomalous Release from Swellable Devices," Journal of Controlled Release (1987) 5:37-42.
Rostovtsev, V.V. et al., "A Stepwise Huisgen Cycloaddition Process: Copper(I)-Catalyzed Regioselective 'Ligation' of Azides and Terminal Alkynes," Angew. Chem. Int. Ed. (2002) 41(14):2596-2599.
Rowe et al., "Handbook of Pharmaceutical Excipients," 6th edition, 2009, Pharmaceutical Press, pp. 110-114 and pp. 581-585. (Year: 2009).
Ruoslahti, E. et al., "Targeting of drugs and nanoparticles to tumors," The Journal of Cell Biology (2010) 188 (6):759-768.
Rupprecht, A., "Wet Spinning of Hyaluronic Acid. Preparation of Oriented Samples," Acta. Chem. Scand. vol. B33, No. 10, 1979, pp. 779-780.
Saettone et al., "Evaluation of muco-adhesive properties and in vivo activity of ophthalmic vehicles based on hyaluronic acid," 1989, International Journal of Pharmaceutics, vol. 51, pp. 203-212. (Year: 1989).
Sahiner, N. et al., "Fabrication and characterization of cross-linkable hydrogel particles based on hyaluronic acid: potential application in volcal fold regeneration", Journal of Biomaterials Science, Polymer Edition, vol. 19, Issue 2, pp. 223-243.
Schante, C.E. et al., "Chemical modifications of hyaluronic acid for the synthesis of derivatives for a broad range of biomedical applications," Carbohydrate Polymers (2011) 85:469-489.
Scott, J.E. et al., "Periodate Oxidation of Acid Polysaccharides", Histochemie, Apr. 26, 1969, vol. 19, pp. 155-161.
Scott, J.E. et al., "Secondary and tertiary structures of hyaluronan in aqueous solution, investigated by rotary shadowing—electron microscopy and computer simulation," J. Biochem vol. 274, 1991, pp. 699-705.
Sedova, P. et al., "Preparation of hyaluronan polyaldehyde—a precursor of biopolymer conjugates," Carbohydrate Research (2013) 371:8-15.
Seidlits, S.K. et al., "The effects of hyaluronic acid hydrogels with tunable mechanical properties on neural progenitor cell differentiation" Biomaterials (2010) 31:3930-3940.
Shang, J. et al., "Chitosan-based electroactive hydrogel," Polymer (2008) 49:5520-5525.
Sheehan, J.K. et al., "X-ray Diffraction Studies on the Connective Tissue Polysaccharides," J. Mol. Biol. (1975) 91:153-163.
Shen, Yan et al., "Synthesis and characterization of low molecular weight hyaluronic acid-based cationic micelles for efficient siRNA delivery," Carbohydrate Polymers (2009) 77(1):95-104.
Shen, Yi et al., "Synthesis, Characterization, Antibacterial and Antifungal Evaluation of Novel Monosaccharide Esters," Molecules (2012) 17(7):8661-8673.
Shimizu, M. et al., "Studies on hyaluronidase, chondroitin sulphatase, proteinase and phospholipase secreted by Candida species", MYCOSES (1996) 39:161-167.
Shutava, T. et al., "Microcapsule Modification with Peroxidase—Catalyzed Phenol Polymerization," Biomacromolecules (2004) 5(3):914-921.
Sieburth, S.M. et al., "Fusicoccin Ring System by [4+4] Cycloaddition. 2. A Model Study," Tetrahedron Letters (1999) 40:4007-4010.
Sieburth, S.M. et al., "The [4+4] Cycloaddition and its Strategic Application in Natural Product Synthesis," Tetrahedron (1996) 52(18):6251-6282.
Slaughter, B.V. et al., "Hydrogels in Regenerative Medicine," Advanced Materials (2009) 21(32-33):3307-3329.
Slezingrova, K. et al., "Synteza a charakterizace palmitoyl hyaluronanu," Chemicke Listy (2012) 106:554-567.
Smeds, K.A. et al., "Photocrosslinkable polysaccharides for in situ hydrogel formation," J. Biomed. Mater. Res. (2001) 64:115-121.
Smejkalova, D. et al., "Structural and conformational differences of acylated hyaluronan modified in protic and aprotic solvent system," Carbohydrate Polymers (2012) 87(2):1460-1466.
Staskus, P.W. et al., "Double-Stranded Structure for Hyaluronic Acid in Ethanol-Aqueous Solution As Revealed by Circular Dichroism of Oligomers," Biochemistry vol. 27, No. 5, 1988, pp. 1528-1534.
Su, W.Y. et al., "Injectable oxidized hyaluronic acid/adipic acid dihydrazide hydrogel for nucleus pulposus regeneration," Acta. Biomater. (2010) 6(8):3044-3055.
Svanovsky, E. et al., "The effect of molecular weight on the biodistribution of hyaluronic acid radiolabeled with 111-In after intravenous administration to rats," Eur. J. Drug Metab. Ph. 2008, vol. 33, No. 3, pp. 149-157.
Tan, H et al., "Injectable in situ forming biodegradable chitosan-hyaluronic acid based hydrogels for cartilage tissue engineering," Biomaterials (2009) 30(13):2499-2506.
Tan, X. et al., "A NIR heptamethine dye with intrinsic cancer targeting, imaging and photosensitizing propeties," Biomaterials (2012) 33:2230-2239.
Tankam, P.F. et al., "Alkynyl polysaccharides: synthesis of propargyl potato starch followed by subsequent derivatizations," Carbohydrate Research (2007) 342:2049-2060.
Tao, Y. et al., "Core cross-linked hyaluronan-styrylpyridinium micelles as a novel carrier for paclitaxel," Carbohydrate Polymers (2012) 88(1):118-124.
Testa, G. et al., "Influence of dialkyne structure on the properties of new click-gels based on hyaluronic acid," International Journal of Pharmaceutics (2009) 378:86-92.
Thakar, D. et al. "A quartz crystal microbalance method to study the terminal functionalization of glycosaminoglycans," Chemical Communications (2014) 50(96):15148-15151.
Thelin, M. et al., "Biological functions of iduronic acid in chondroitin/dermatan sulfate," FEBS Journal (2013) 280:2431-2446.
Thomas et al, "Hyaluronic acid conjugated superparamagnetic iron oxide nanoparticle for cancer diagnosis and hyperthermia therapy," Carbohydrate Polymers 131 (2015) pp. 439-446.
Til, H.P. et al., "Acute and Subacute Toxicity of Tyramine, Spennidine, Spennine, Putrescine and Cadaverine in Rats," Food and Chemical Toxicology (1997) 35(3-4):337-348.

(56) References Cited

OTHER PUBLICATIONS

Tonelli, A.E., "Effects of crosslink density and length on the number of intramolecular crosslinks (defects) introduced into a rubbery network," Polymer (1974) 15(4):194-196.
Tornoe, C. et al., "Peptidotriazoles on Solid Phase: [1,2,3]—Triazoles by Regiospecific Copper(I)—Catalyzed 1,3-Dipolar Cycloadditions of Terminal Alkynes to Azides," J. Org. Chem. (2002) 67:3057-3064.
Um, I.C. et al., "Electro-Spinning and Electro-Blowing of Hyaluronic Acid," Biomacromolecules (2004) 5:1428-1436.
Uyama, H. et al., "Enzymatic Synthesis of Polyphenols," Current Organic Chemistry (2003) 7:1387-1397.
Van Bommel, K.J.C. et al., "Responsive Cyclohexane-Based Low-Molecular-Weight Hydrogelators with Modular Architecture," Angew. Chem. Int. Ed. (2004) 1663-1667.
Veitch, N. C., "Horseradish peroxidase: a modem view of a classic enzyme," Phytochemistry (2004) 65:249-259.
Wang, J. et al., "Polymeric Micelles for Delivery of Poorly Soluble Drugs: Preparation and Anticancer Activity In Vitro of Paclitaxel Incorporated into Mixed Micelles Based on Poly(ethylene Glycol)-Lipid Conjugate and Positively Charged Lipids," Journal of Drug Targeting (2005) 13(1):73-80.
Wang, W. et al., "Developing Fluorescent Hyaluronan Analogs for Hyaluronan Studies," Molecules 2012, 17, 1520-1534.
Wang, X. et al., "Formation of water-resistant hyaluronic acid nanofibers by blowing-assisted electro-spinning and non-toxic post treatments," Polymer (2005) 46:4853-4867.
Weng L., et al., "Self-crosslinkable hydrogels composed of partially oxidized hyaluronan and gelatin: In vitro and in vivo responses," Journal of Biomedical Materials Research Part A, 85:352-365.
Weng, L. et al., "In vitro and in vivo suppression of cellular activity by guanidinoethyl disulfied released from hydrogel microspheres composed of partially oxidized hyaluronan and gelatin," Biomaterials, Aug. 3, 2008, vol. 29, pp. 4149-4156.
Wermuth, C.G., "Similarity in drugs: reflections on analogue design," Drug Discovery Today (2006) 11(7/8):348-354.
Werner, T. et al., "Simple Method for the Preparation of Esters from Grignard Reagents and Alkyl 1-Imidazolecarboxylates," J. Org. Chem. (2006) 71(11):4302-4304.
Won, K. et al., "Horseradish Peroxidase-Catalyzed Polymerization of Cardanol in the Presence of Redox Mediators," Biomacromolecules (2003) 5(1), 1-4.
Wondraczek, H. et al., "Synthesis of highly functionalized dextran alkyl carbonates showing nanosphere formation," Carbohydrate Polymers (2011) 83:1112-1118.
Written Opinion in International Patent Application No. PCT/CZ2009/000131, dated Apr. 9, 2010, 3 pgs.
Written Opinion in International Patent Application No. PCT/CZ2010/000030, dated Sep. 1, 2010, 4 pgs.
Written Opinion in International Patent Application No. PCT/CZ2010/000128, dated Jun. 9, 2011, 4 pgs.
Written Opinion in International Patent Application No. PCT/CZ2010/000129, dated Jun. 15, 2011, 4 pgs.
Written Opinion in International Patent Application No. PCT/CZ2011/000126, dated Apr. 12, 2012, 4 pgs.
Written Opinion in International Patent Application No. PCT/CZ2012/000035, dated Aug. 28, 2012, 4 pgs.
Written Opinion in International Patent Application No. PCT/CZ2013/000023, dated Aug. 9, 2013, 3 pgs.
Written Opinion in International Patent Application No. PCT/CZ2013/000057, dated Jul. 24, 2013, 4 pgs.
Written Opinion in International Patent Application No. PCT/CZ2013/000063, dated Apr. 23, 2015, 9 pgs.
Written Opinion in International Patent Application No. PCT/CZ2013/000091, dated Oct. 31, 2013, 4 pgs.
Written Opinion in International Patent Application No. PCT/CZ2013/000116, dated Jan. 28, 2014, 5 pgs.
Written Opinion in International Patent Application No. PCT/CZ2013/000155, dated Feb. 19, 2014, 6 pgs.
Written Opinion in International Patent Application No. PCT/CZ2013/000156, dated Apr. 4, 2014, 7 pgs.
Written Opinion in International Patent Application No. PCT/CZ2013/000157, dated Mar. 19, 2014, 6 pgs.
Written Opinion in International Patent Application No. PCT/CZ2013/000158, dated Mar. 19, 2014, 7 pgs.
Written Opinion in International Patent Application No. PCT/CZ2014/000138, dated May 4, 2015, 5 pgs.
Written Opinion in International Patent Application No. PCT/CZ2015/000018, dated Jul. 22, 2015, 8 pgs.
Written Opinion in International Patent Application No. PCT/CZ2015/000068, dated Jan. 8, 2016, 6 pgs.
Written Opinion in International Patent Application No. PCT/CZ2016/000027, dated Jun. 27, 2016, 6 pgs.
Written Opinion in International Patent Application No. PCT/CZ2016/000065, dated Sep. 30, 2016, 5 pgs.
Written Opinion in International Patent Application No. PCT/CZ2016/050036, dated Feb. 6, 2017, 6 pgs.
Written Opinion in International Patent Application No. PCT/CZ2016/050048, dated May 3, 2017, 6 pgs.
Written Opinion in International Patent Application No. PCT/EP2016/064653, dated Aug. 25, 2016, 6 pgs.
Xu, Y. et al., "Feasibility study of a novel crosslinking reagent (alginate dialdehyde) for biological tissue fixation," Carbohydrate Polymers (2012) 87(2):1589-1595.
Xu, Y.-P. et al., "Kinetics of Phenolic Polymerization Catalyzed by Peroxidase in Organic Media," Biotechnology and Bioengineering (1995) 47(1):117-119.
Yamane, Shintaro et al., "Feasibility of chitosan-based hyaluronic acid hybrid biomaterial for a novel scaffold in cartilage tissue engineering," Biomaterials (2005) 26(6);611-619.
Yang, Rui-Meng et al., "Hylauronan-modified superparamagnetic iron oxide nanoparticles for bimodal breast cancer imaging and photothermal therapy," Int'l J. of Nanomedicine 2017: 12, pp. 197-206.
Yao, F. et al., "A Novel Amphoteric, pH-Sensitive, Biodegradable Poly[chitosan-g-(L-lactic-co-citric) acid] Hydrogel," Journal of Applied Polymer Science (2003) 89:3850-3854.
Ye, Y. et al., "Multivalent Carbocyanine Molecular Probes: Synthesis and Applications," Bioconjugate Chem. 2005, 16, 51-61.
Ye, Y. et al., "Novel Near-Infrared Fluorescent Integrin-Targeted DFO Analogue," Bioconjugate Chem. (2008) 19:225-234.
Ye, Y. et al., "Polyvalent Carbocyanine Molecular Beacons for Molecular Recognitions," J. Am. Chem. Soc. 2004, 126, 7740-7741.
Ye, Y.; et al., "Integrin Targeting for Tumor Optical Imaging," Theranostics 2011, 1, 102-126.
Yeom, J. et al., "Effect of Cross-Linking Reagents for Hyaluronic Acid Hydrogel Dermal Fillers on Tissue Augmentation and Regeneration," Bioconjugate Chemistry (2010) 21(2):240-247.
Zaafarany, I. et al., "Oxidation of Some Sulfated Carbohydrates: Kinetics and Mechanism of Oxidation of Chondroitin-4-Sulfate by Alkaline Permanganate with Novel Synthesis of Coordination Biopolymer Precursor," J. Mat. Sci. Res. (2013) 2(4):23-36.
Zeng, J. et al., "Photo-Induced Solid-State Crosslinking of Electrspun Poly(vinyl alcohol) Fibers," Macromolecular Rapid Communications (2005) 26:1557-1562.
Zeng, Yuan-Xian et al., "Preparation and Enhancement of Thermal Conductivity of Heat Transfer Oil-Based MoS2 Nlanofluids," Journal of Nanomaterials, vol. 2013, Art. ID 270490, 6 pgs.
Zhong, S.P. et al., "Biodegradation of hyaluronic acid derivatives by hyalurondiase," Biomaterials (1994) 15 (5):359-365.
Zou, X.H. et al., "Specific interactions between human fibroblasts and particular chondroitin sulfate molecules for wound healing," Acta Biomaterialia (2009) 5(5):1588-1595.

DERIVATIVES OF SULFATED POLYSACCHARIDES, METHOD OF PREPARATION, MODIFICATION AND USE THEREOF

FIELD OF THE INVENTION

The invention relates to derivatives of sulfated polysaccharides having a conjugated double bond in the 4th and 5$^{th}$ position of the galactopyranose ring situated in the 6$^{th}$ position with respect to the aldehyde. Further, the invention relates to the method of preparation, modification and use thereof.

BACKGROUND OF THE INVENTION

Glycosaminoglycans are linear polysaccharides consisting of aminohexose and uronic acid, except of keratin sulfate. They form a large part of intracellular matrix of connective tissue, in particular cartilage, ligaments and tendons. Sulfated polysaccharides, e.g. chondroitin sulfate or dermatan sulfate, are also, besides hyaluronic acid, important examples of glycosaminglycanes.

Chondroitin sulfate is a linear, sulfated, and negatively charged glycosaminoglycan composed of recurrent monomer units of N-acetyl-D-galactosamine and D-glucuronic acid attached to each other via β(1→3) and β(1→4) O-glycosidic bonds (the structural formula of chondroitin sulfate see below).

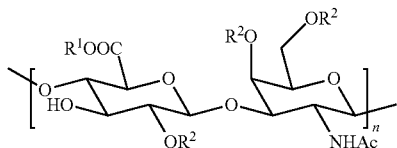

where
R$^1$ is H or Na,
R$^2$ is H, —SO$_2$—OH, or —SO$_2$—ONa

Chondroitin sulfate derives from animal connective tissues, where it binds to proteins and thus forms a part of proteoglycans. The sulfation of chondroitin is realized by means of sulfotransferases in various positions and of various kinds. The unique sulfation pattern of particular positions in the polymer chain encodes the specific biological activity of chondroitin sulfate. Chondroitin sulfate is an important building component of cartilage in joints, conferring them the compression resistance and restoring the balance of the joint lubricant composition (Baeurle S. A., Kiselev M. G., Makarova E. S., Nogovitsin E. A. 2009. *Polymer* 50: 1805). Together with glucosamine, chondroitin sulfate is used as nutritional supplement for treating or prevention of osteoarthritis in humans (e.g. Flextor®, Advance Nutraceutics, Ltd.) or animals (e.g Geloren$^{dog}$ ®, Contipro Pharma, Ltd.). From the pharmaceutical point of view, chondroitin sulfate is considered to be a drug with delayed response for pain control at degenerative diseases of joints (Aubry-Rozier B. 2012. *Revue Médicale Suisse* 14: 571).

Dermatan sulfate is linear, sulfated, and negatively charged glycosaminoglycan composed of repeating monomer units of N-acetyl-D-galactosamine and L-iduronic acid attached to each other via β(1→3) and β(1→4) O-glycosidic bonds (the structural formula of dermatan sulfate see below).

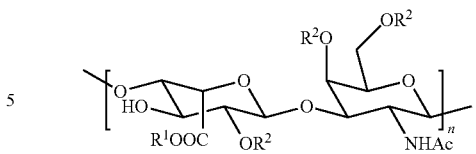

where
R$^1$ is H or Na,
R$^2$ is H, —SO$_2$—OH, or —SO$_2$—ONa

Dermatan sulfate differs from chondroitin sulfate by the presence of L-iduronic acid, which is a C5 epimer of D-glucuronic acid. The inverse configuration of iduronic acid allows a better flexibility of dermatan sulfate chains and ensures their specific interaction of glycosamine-glycoprotein in the surrounding area. These interactions contribute to the regulation of several cell processes, such as migration, proliferation, differentiation, or angiogenesis. The transformation of chondroitin sulfate into dermatan sulfate is provided by means of three enzymes: dermatan sulfate epimerase 1 (DS-epi1), dermatan sulfate epimerase 2 (DS-epi2), and dermatan 4-O-sulfotransferase (D4ST1). The epimerisation reaction of glucuronic acid into iduronic acid, together with the way of the sulfation, is not random but specifically enzymatically controlled, which results in encoding the information concerning the function of the construed glycosaminoglycan (Thelin M., et al. 2013. *FEBS Journal* 280: 2431).

Carrageenans are a group of linearly sulfated polysaccharides obtained by the extraction of red marine algae. Galactose and its 3,6-anhydroderivative, that are associated to each other via α(1→3) or β(1→4) O-glycosidic bonds, are their basic building units. There are three main types of carrageenan, which differ in their degree of sulfation and water solubility. Kappa-carrageenan has one sulfate per dimer and forms rigid gels in water. Iota-carrageenan comprises two sulfates and forms soft gels, whereas lambda-carrageenan with three sulfates does not exhibit gel forming properties. Carrageenan is an alternative of animal gelatine for vegetarians and vegans. It is used for thickening and stabilization of food products and as an emulsifier in pharmaceutical and textile industry.

Oxidation of Glycosaminoglycans

Thanks to their functional diversity, the polysaccharides can be oxidized in various positions (Cumpstey I., 2013. *ISRN Organic Chemistry*, 1). In the case of glycosaminegly-canes there are three ways of oxidation. In the first one, the primary hydroxyl is oxidized to form a carboxylic acid. The combination of TEMPO/NaClO is used for the oxidation the most often (Jiang B., et al. 2000. *Carbohydrate Research* 327: 455; Huang L. et al. 2006. *Chemistry*, 12: 5264). Due to the steric bulkiness of TEMPO, this method is regioselective for primary hydroxyls only.

On the contrary, the second way leads to the oxidation of secondary hydroxyls to form diketone compounds. In this case, as the oxidation agents the oxides of transition metals based on Cr(VI) (Hassan R., et al. 2013. *Carbohydrate Polymers*, 92: 2321) or Mn (VII) (Gobouri A. A., et al. 2013. *International Journal of Sciences*, 2:1; Zaafarany I. A., et al. 2013. *Journal of Materials Science Research*, 2: 23) are used.

The third type of oxidation is based on periodate (IO$_4$$^-$) oxidation which also attacks secondary hydroxyl groups but simultaneously the pyranose ring breaks (Dawlee S. et al. 2005. Biomacromolecules, 6: 2040; Liang Y., et al. 2011.

*Colloids and Surfaces B: Biointerfaces,* 82: 1; Xu Y., et al. 2012. *Carbohydrate Polymers,* 87: 1589). During the oxidation, dialdehyde forms first and then it is further oxidized to dicarboxylic acid.

All afore mentioned ways of the oxidation have several drawbacks. In case of the oxidation with the use of TEMPO/NaClO, the formation of polyuronic acid is favoured instead of the desired C6-aldehyde. The reaction conditions for the aldehyde level need to be optimized, as it was demonstrated in the case of hyaluronic acid (Buffa R., et al., WO2011069475, Šedová P., et al., 2013. *Carbohydrate Research,* 371: 8). In addition, a higher content of carboxylic groups in the polymer significantly influences the conformation, interaction, and recognizing the polysaccharide with the biological surrounding (Zou X. H., et al. 2009. *Acta Biomaterialia,* 5: 1588).

Even though a chemoselective course of the reaction can be achieved periodate oxidation, this way is not preferred due to the dramatic decrease of the molecular weight of the polymer and irreversible cleavage of the pyranose ring, which results in the loss of the native character of the polysaccharide.

As regards the use of the oxidation agents derived from the transition metal oxides, the oxidized polysaccharides cannot be used for biomedical applications because of their high toxicity (Normandin L., et al. 2002. *Metabolic Brain Disease,* 17: 375; Katz S. A., et al. 2006. *Journal of Applied Toxicology,* 13: 217).

Dehydration Reactions of Oxidized Derivatives of Polysaccharides

The presence of an aldehyde in the polysaccharide structure results in an acid character of the hydrogen atom in the adjacent α-position. This hydrogen becomes easily accessible under basic conditions for elimination reactions to form a carbanion, which is stabilized by the conjugation with the adjacent aldehyde and thus displaces the leaving group in the β-position (way a, Scheme 1). The elimination can proceed also under acid conditions, where the activation of the leaving group occurs first to form a carbanion in the β-position (way b, Scheme 1). In the reaction mixture, the carbanion is neutralized with a free electron pair in the α-position. The third possible way can be performed without the addition of a base or an acid, using a simultaneous elimination of a molecule (way c, Scheme 1).

patent (Buffa et al.: CZ304512). The authors describe the preparation of α,β-unsaturated aldehyde of hyaluronan and its use in cross-linking reactions. The disclosed synthesis involves the use of sterically voluminous organic bases (e.g. diisopropylamine, trimethylamine), inorganic bases, e.g. $Ca(OH)_2$ in the mixture of water-organic solvent of the type of DMSO, sulfolane in the ratio of 3/1 to 1/2 under higher temperatures of 50-60° C. The dehydration is also performed in solid state by heating the polymer to 50-100° C. for 4-5 days. The authors describe the oxidation and dehydration of hyaluronic acid in two steps and they do not describe the direct dehydration during the oxidation step. This solution has an important drawback of two steps synthesis and the use of inappropriate reaction conditions in the presence of caustic (corrosive) elimination agents, presence of an organic solvent, necessity of an elevated temperature, and a long reaction time. All these parameters cause the synthesis to be more expensive and more complicated from the technological point of view (e.g. the corrosion of production apparatus, difficult purification of the product, higher price of dipolar aprotic solvents such as DMSO, sulfolane, and elimination agents such as $Et_3N$ and DIPEA, a high consumption of energy and cooling water, a higher risk of dangerous residues in the product, the product biocompatibility at risk, a higher rate of polymer degradation due to the basic environment and higher temperature). The said drawbacks of the synthesis of α,β-unsaturated aldehyde of HA in CZ304512 are, according to this invention, successfully overcome, as the synthesis proceeds in one pot without the necessity to isolate the intermediate product in the form of a saturated C6-aldehyde, without adding the elimination agent, without adding the organic solvent, under room temperature and with the reaction times in the order of hours.

Cross-Linking Reaction of Oxidized Polysaccharides

The introduction of an aldehyde into the polysaccharide structure allows an additional modification of the polymer chain with the aid of nucleophilic addition. Several patent documents describing the binding of amines to aldehydes are known. A typical exemplary reaction for glycosaminoglycans is the reaction of dialdehyde formed by the oxidation with periodate with various low molecular (amines, hydrazides, alkoxyamines, semicarbazides) or polymeric N-nucleophiles (gelatine, chitosan), or S-nucleophiles Scheme 1. Elimination reaction in the aldehyde structure: (a) formation of a carbanion by the treatment with a base, mechanism E1cb (b) formation of a carbanion by the treatment with an acid, mechanism E1 (c) simultaneous elimination, mechanism E2.

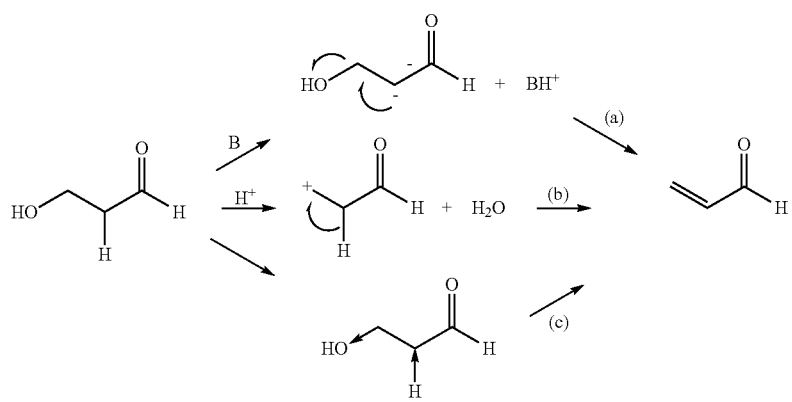

A targeted dehydration of aldehyde of hyaluronan in the 6th position in the glucosamine ring was described in the (thiols, aminothiols) to prepare biocompatible hydrogels (Dawlee S., et al. 2005. *Biomacromolecules,* 6: 2040; Weng L., et al. 2008. *Journal of Biomedical Materials Research part A*, 85: 352, Bergman K., et al.: WO2009/108100, Hilborn J., et al.: WO2010/138074). The cross-linking of aldehyde of hyaluronic acid prepared with the use of Dess-Martin periodinane or with the use of the combination of TEMPO/NaClO with various amines was described in patent documents (Buffa R., et al.: WO2011069474; Buffa R., et al.: WO2011069475). α,β-Unsaturated aldehyde of hyaluronic acid was prepared by the dehydration of C6-aldehyde in N-acetyl-D-glucosamine subunit (Buffa R., et al: CZ304512). In addition to oxidized derivatives of hyaluronic acid, the authors describe also its use in reactions with aliphatic, aromatic amines having an optional content of N, S, or O atoms. However, they are prepared under high temperatures and with the use of corrosive elimination agents, which is considerably unfavourable for maintaining their biological activity due to their possible denaturation and the presence of byproducts. Further, the cross-linking reactions of α,β-unsaturated aldehyde of hyaluronic acid with deacetylated polysaccharides as a multifunctional amino linker are mentioned to illustrate the advantages of the conjugation of the aldehyde from the polysaccharide influencing the rheological properties of the prepared hydrogels. However, the hydrogels prepared in this way do not show satisfactory mechanical properties, especially as far as the hydrogel rigidity is concerned.

SUMMARY OF THE INVENTION

The aim of the invention is the preparation of sulfated polysaccharides under mild reaction conditions, in a shorter time, and without the use of undesirable impurities of elimination agents or organic solvents. This method prevents the significant degradation and loss of biological properties of sulfated polysaccharides, which are important for tissue engineering, regenerative medicine, or biomedical applications. The object of the invention consists in the derivatives of sulfated polysaccharides having, as a part of their polymer chain, at least one galactopyranose ring modified according to the general formula I or II, said ring containing a double bond in the $4^{th}$ and $5^{th}$ position with a conjugated aldehyde or its hydrated form respectively (general formula II)

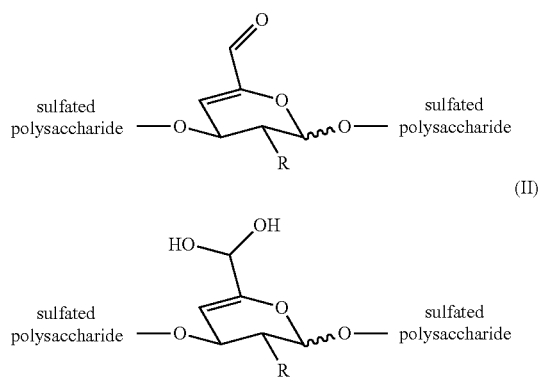

where
R is OH, O—SO$_2$—OH, O—SO$_2$—ONa, or NH—C(O)—CH$_3$.

A necessary condition is the use of sulfated polysaccharides containing at least one galactopyranose ring in their chain, this ring being sulfated in the $4^{th}$ position, and simultaneously bound in the chain via α (1→3) or β (1→3) O-glycosidic bond according to the general structural formula III.

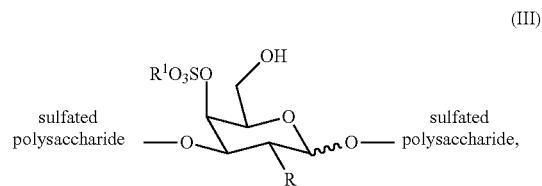

where
R is OH, O—SO$_2$—OH, O—SO$_2$—ONa, or NH—C(O)—CH$_3$
R$^1$ is H, or Na.

The polysaccharide is preferably selected from the group comprising chondroitin sulfate, dermatan sulfate, carrageenan, and their pharmaceutically acceptable derivatives and/or salts, and its molecular weight is preferably in the range of $1\times10^3$ to $5\times10^4$ g·mol$^{-1}$, and the degree of the substitution in the range of 1 to 40%, preferably 10 to 25%. In the formula I or II respectively, the term "degree of substitution" refers to the degree of the modification to an unsaturated aldehyde, or its hydrated form respectively.

This solution enables to stabilize the conjugates of sulfated polysaccharides with amines by means of the multiple bond from the aldehyde, so a substantially wider range of amines can be bound more stably on the polysaccharides modified in this way (Scheme 2), under physiological conditions.

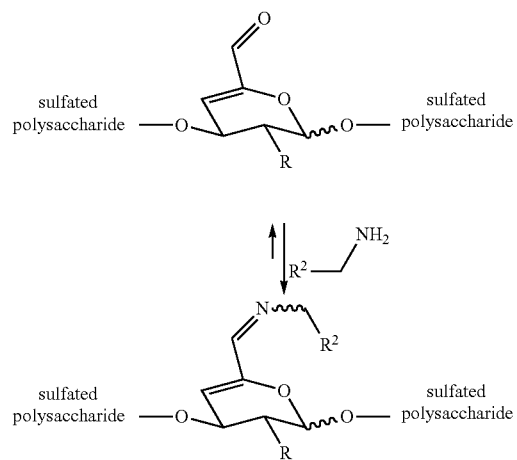

where
R is OH, O—SO$_2$—OH, O—SO$_2$—ONa, or NH—C(O)CH$_3$
R$^2$ is alkyl, aryl, hetaryl.
Scheme 2. Binding of Amine to α,β-Unsaturated Aldehyde of Sulfated Polysaccharide.

Further, the invention relates to the method of preparation of a derivative of the general structural formula I or II, where the sulfated polysaccharide, which is water soluble in its native form and contains, in its structure, at least one galactopyranose unit sulfated in the $4^{th}$ position, this unit being bound in the polymer chain via α (1→3) or β (1→3) O-glycosidic bond, is first oxidized to an aldehyde in the $6^{th}$ position and immediately after the oxidation in the current reaction mixture provides an α,β-unsaturated aldehyde via the direct elimination (Scheme 3).

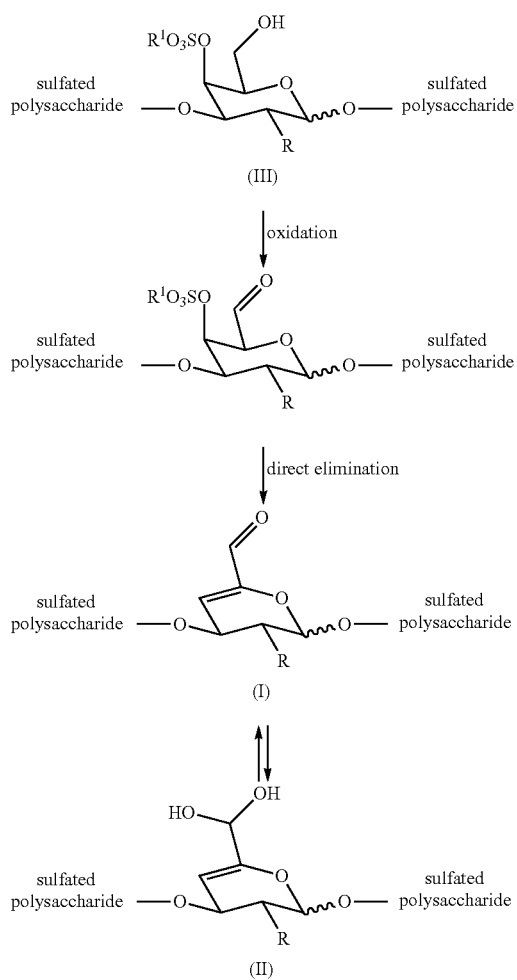

where
R is OH, O—SO$_2$—OH, O—SO$_2$—ONa, or NH—C(O)CH$_3$
R$^1$ is H or Na.
Scheme 3. Method of Preparation of an α,β-Unsaturated Aldehyde in the Structure of the Sulfated Polysaccharide.

The selective oxidation of the primary hydroxyl group in the 6$^{th}$ position of galactopyranose can be realized e.g. by means of the oxidation system of 2,2,6,6-tetramethyl-1-piperidinyloxy radical R$^3$-TEMPO/NaClO, where R$^3$ is hydrogen or N-acetyl, in water or an aqueous solution of inorganic salts. Preferably, this step proceeds in water, under the temperature of 5 to 25° C., more preferably 5 to 10° C., the molar amount of NaClO is within the range of 0.1 to 2.0 equivalent, and the molar amount of R$^3$-TEMPO is within the range of 0.01 to 0.2 equivalent, with respect to a sulfated polysaccharide dimer. The molecular weight of the initial sulfated polysaccharide is within the range of 1×10$^4$ to 5×10$^6$ g·mol$^{-1}$, and it must contain galactopyranose units sulfated in the 4$^{th}$ position, and it is bound via α (1→3) or β (1→3) O-glycosidic bonds in the polymer chain. Preferably, the initial sulfated polysaccharide is chondroitin sulfate, dermatan sulfate, carrageenan, or their pharmaceutically acceptable derivative and/or salt. The aqueous solution of salts may be e.g. an aqueous solution comprising an alkaline metal salt and/or a buffer, e.g. PBS.

The elimination reaction of the oxidized and sulfated polysaccharide proceeds immediately after the oxidative stage in the same reaction mixture without the need of adding an elimination agent, especially an acid or a base, an organic solvent, or without elevation of the reaction temperature, and without the isolation of the saturated C6-aldehyde in galactopyranose subunit being sulfated in 4$^{th}$ position. The elimination reaction proceeds in water or in aqueous solutions of inorganic salts (e.g. alkali metals salts), or buffers (e.g. PBS) at the temperature of 5-25° C. and there is no need of an additional reaction time. Further, the elimination stage is proportional to the achieved oxidation stage in the reaction mixture. The method of preparation of the α,β-unsaturated aldehyde integrates two reaction steps (oxidation and elimination) into one pot without the isolation of the intermediate from the oxidation stage. The oxidation results in an α,β-unsaturated aldehyde instead of a saturated C6-aldehyde in the structure of sulfated polysaccharide. In comparison to the method of the preparation of an α,β-unsaturated aldehyde of hyaluronic acid (Buffa R et al.: CZ304512), the presented approach is different and definitely advantageous in the parameters listed in Table 1.

TABLE 1

Differences in the preparation of α,β-unsaturated aldehydes in comparison with the prior art

| Parameter | CZ304512 | Invention |
| --- | --- | --- |
| Polysaccharide type | Hyaluronic acid | Sulfated polysaccharides |
| Number of steps of the synthesis | 2 | 1 |
| Elimination agent | yes (10-15 equivalents) | no |
| Solvent | water-organic solvent mixture | water |
| Reaction temperature | 50-100° C. | Room temperature - 5-25° C. |
| Reaction time | 2-5 days | 1-2 h |
| Degree of substitution | 5-7% | 20-25% |

Table 1 above clearly shows that the method of preparation of sulfated polysaccharide derivatives according to the invention results directly in the formation of α,β-unsaturated aldehydes instead of their saturated analogues. Another difference of the presented method of the invention consists in that it is not applicable to the polysaccharides mentioned in the prior art, because the presence of the sulfate is necessary for the process. Other advantages address to the reaction proceeding exclusively in water, without the need of addition of any organic solvent or any elimination agent. Furthermore, the reaction proceeds at room temperature (20-25° C.) with short reaction times (1-2 h) without isolation of the saturated C6-aldehyde. The above mentioned method results in derivatives of sulfated derivatives having the general formulae I and/or II, DS within the range of 20 to 25%. The method of their preparation is technologically interesting and substantially more preferable from the temporal and cost point of view in comparison with the known methods.

Considering the chemical modification, the α,β-unsaturated aldehyde in the sulfated polysaccharides can be used mainly for condensation reactions with various N-nucleophiles. The aldehyde, in the role of the reactive electrophilic centre, maintains its stability and reactivity also in water, which can be preferably used for the mentioned binding (conjugation) of biocompatible amines with the derivatives of the general formulae I and II. The term "amine" is well known to a person skilled in the art, and it can represent, without any limitation, alkyl amine, aryl amine, hetaryl amine, amino acid, peptide, or polymer with a free amino group. The latter can be directly incorporated into the polymer or is bound via a suitable linker that can be linear or branched, optionally containing N, S, or O atoms. The term "polymer with an amino group" is understood to be a deacetylated polysaccharide, protein, peptide, or another biopolymer or biocompatible synthetic polymer.

Thus, the invention further relates to the method of modification of the derivative of the general formula I or II, where the derivative reacts with an amine of the general formula $R^2$—$NH_2$, where $R^2$ is alkyl, aryl, hetero aryl, linear or branched $C_1$ to $C_{30}$ chain, optionally containing N, S, or O atoms. The amine is preferably a biologically active amine, particularly amino acid or peptide, or a biologically acceptable polymer containing a free amino group, where this amino group is an inherent part of the polymer (e.g. gelatine, chitosan, deacetylated hyaluronic acid, deacetylated chondroitin sulfate, etc.) or is bound to the polymer via a linker containing amino, hydrazine, hydrazide, amino alkoxy, hydroxyl, carboxyl, thiol group or any combination thereof. The molar amount of amine can be, preferably, within the range of 0.05-3 equivalents with respect to a dimer of the sulfated polysaccharide. The binding of amine can proceed in water, phosphate buffer, or water-organic solvent system at the temperature in the range of 20 to 60° C. for 10 minutes to 150 h. A suitable organic solvent is understood to be a water miscible alcohol, preferably isopropanol or ethanol, and water miscible aprotic solvents, preferably dimethyl sulfoxide, wherein their content in the reaction mixture does not exceed 50% (v/v). The reaction with amine can be preferably performed under physiological conditions (pH=7.4 and T=37° C.). Besides amines, the reaction proceeds also with other N-nucleophiles containing an amino group in their structure, such as hydrazines, hydroxyl amines, hydrazides, semicarbazides, or thiosemicarbazides. In case of a reaction with monofunctional N-nucleophiles, they are bound to the polymer, wherein the use of bi- and polyfunctional N-nucleophiles provides cross-linking of polymer chains, i.e. the formation of hydrogels. Depending on the type of the N-nucleophile used, its amount with respect to the ratio of the binding sites, polymer structure, solution concentration, degree of substitution, and molecular weight of the polymer, cross-linked polymers with wide range of viscoelastic and mechanical properties can be prepared exactly according to the needs of the intended applications in tissue engineering or regenerative medicine. In some specific cases, the reaction of the derivative of the invention with an amine can proceed within the whole range of pH, wherein in other cases the pH value is important for the reaction. A person skilled in the art can recognize it in advance, or determine by means of routine measurements.

The intended applications are meant to be mainly the preparations of scaffolds as bioactive and biodegradable support materials imitating the extracellular matrix. These materials can serve as the carriers for cells or biologically active substances, cell attractants, as the carrier medium for cell delivery to the site of a tissue defect, as a tissue filler, an adequate tissue substitute, or a protective barrier. Other demands put on the functional scaffolds comprise ensuring a suitable chemical and physiological environment for the cell proliferation and differentiation, transport of nutrients and waste products of cell metabolism. Depending on the way of the scaffold application, it is possible to prepare injection scaffolds from the cross-linked sulfated polysaccharides in the form of gel forming solutions, wherein the scaffold and the new tissue form in vivo, or solid scaffolds, which are implanted to an organism after the cell cultivation and formation of the new tissue in vitro. Furthermore, the proper choice of parameters of the cross-linking reaction (concentration and binding sites ratio) enables to achieve short times of gelation, in the order of seconds (see Example 30), which can be preferably used for the gelation in situ at the presence of a biological material, the so-called the cell encapsulation. The cross-linking reaction is illustrated in the Scheme 4:

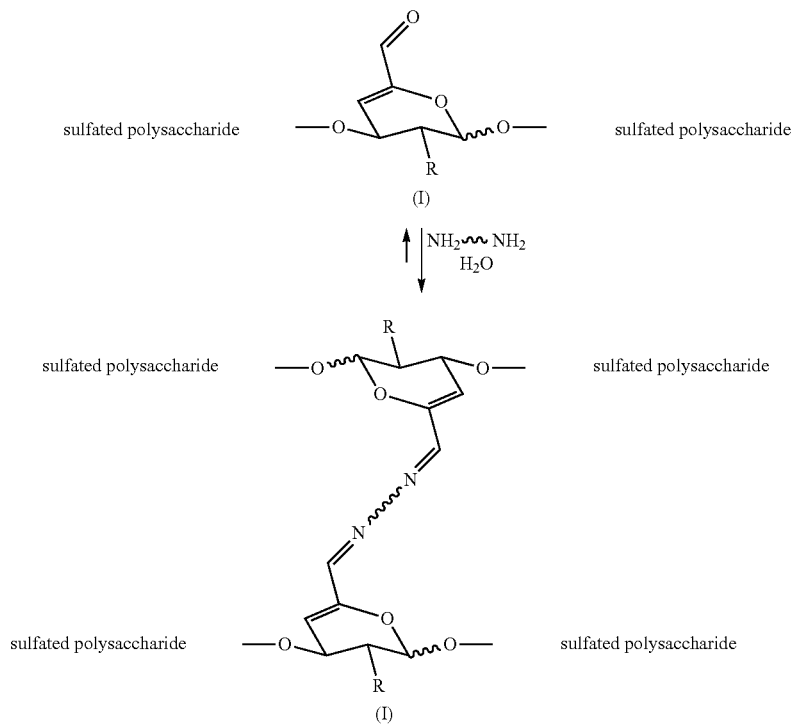

-continued

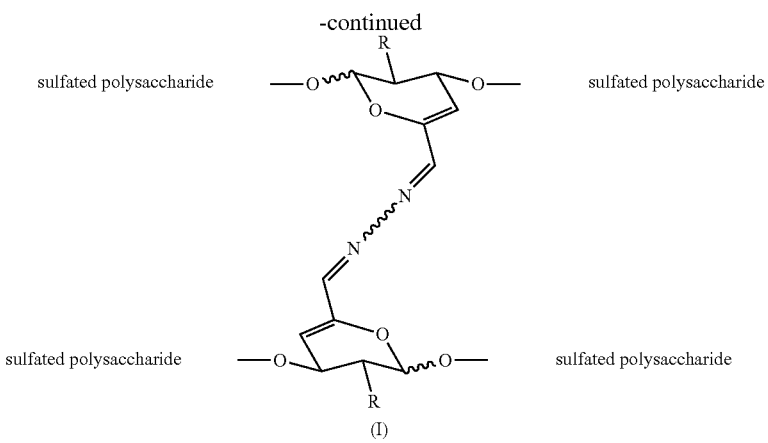

where
R is OH, O—SO₂—OH, O—SO₂—ONa or NH—C(O)CH₃

Scheme 4. Cross-Linking of a Sulfated Polysaccharide by Means of an α,β-Unsaturated Aldehyde and a Diamine.

The higher stability of the bond of an amine with an α,β-unsaturated aldehyde comparing to a conventional saturated aldehyde is ensured by means of the conjugation of the aldehyde with the adjacent double bond. Thus, more stable and better cross-linked materials based on sulfated polysaccharides can be prepared, as was shown by the example of the non-sulfated polysaccharide of hyaluronic acid (Buffa R., et al: CZ304512).

The crosslinking is performed by reacting the derivative with a water soluble biocompatible bi- and polyfunctional N-nucleophile selected from the group comprising alkyl amines, aryl amines, heteroalkyl amines, hetaryl amines, amino acids, peptides, polymers with free amino group, hydrazines, hydroxyl amines, hydrazides, semicarbazides, or thiosemicarbazides, wherein the crosslinking of the derivative proceeds. The preferred nucleophiles comprise hydrazides, dihydrazides, deacetylated polysaccharides, or alkoxyamines. The reaction can preferably proceed in phosphate buffer.

However, the comparative analysis of mechanical properties (Young's modulus of elasticity in compression, elastic limit in compression, and deformation rate of the cross-linked gels) proved a higher density of the gels prepared from the oxidized chondroitin sulfate (see Example 31 of the invention) in comparison with the gels based on the oxidized hyaluronan. The higher rigidity of gels reflects the higher crosslink density in the structure of the polysaccharide, and thus a better volume and shape stability of the crosslinked material is ensured. In addition, better crosslinked materials show less changes in mechanical properties in the course of time and thus meet the needs put on the functional cell scaffold. In this case, more effective crosslinking can be achieved by means of a higher degree of substitution of the α,β-unsaturated aldehyde in the structure of the sulfated polysaccharide (see Table 1 above), which is one of the important advantages of the invention in comparison with the prior art.

The second advantage of more efficiently crosslinked gels consists in a lower rate of swelling in a physiological medium. This can be preferably used for scaffolds in tissue engineering where controlled material performance in a living organism at contact with the tissue is desired, without dramatic changes of their mechanical properties or shape or volume.

The third advantage of the higher degree of substitution of the α,β-unsaturated aldehyde in the structure of the sulfated polysaccharide is the possibility of binding a higher amount of e.g. a biologically active amine. In this way, a higher concentration of the biologically active substance can be achieved at the site of the effect for applications of support systems, for which the described invention can be also preferably used. Furthermore, the proposed method enables binding of a broader variety of biologically active amines (e.g. amino acids, peptides) that can be naturally released in their native (active) form. It was found repetitively in several examples (butylamine, lysine, RGD peptide) that at lower pH the bond amine-α,β-unsaturated aldehyde is less stable (Scheme 5), so the prepared conjugates can be preferably used for drug delivery systems based on pH-responsive biomaterials.

Scheme 5. Stability of imine of α,β-unsaturated aldehyde chondroitin sulfate (DS = 20%) with RGD peptide (aminohexane acid-Gly-Arg-Gly-Asp-NH₂) in water.

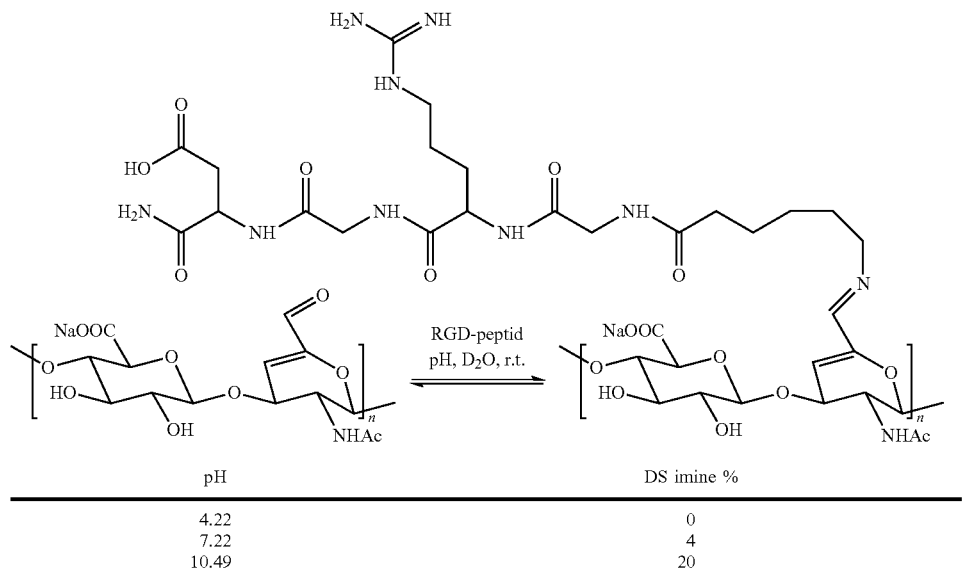

| pH | DS imine % |
|---|---|
| 4.22 | 0 |
| 7.22 | 4 |
| 10.49 | 20 |

More particularly, this stability of an imine based on alkyl, aryl, or hetaryl amine in water can be used as follows: when the conjugate (imine), formed by a biologically active amine (e.g. drug, antiseptic preparation, peptide, amino acid etc.) and polysaccharide (carrier) being stable under moderately basic conditions, is incorporated into the target site of an organism, whose pH is different (neutral or moderately acid), this conjugate is decomposed and the biologically active substance is released in this site.

It was proved that the α,β-unsaturated aldehyde itself in the chondroitin sulfate structure is not cytotoxic (see Example 32 according to the invention), so the conjugates and the crosslinked products of α,β-unsaturated aldehydes of the formula I or II with biocompatible amines are suitable for targeted applications in biomedicine and tissue engineering. These substances are supposed not to influence negatively the cell viability, not to induce an immune reaction in the organism, to be enzymatically degradable, whereas the products of their degradation are biocompatible as well. Thus the derivatives of the formulae I or II can be used for the preparation of supports of biologically active substances in the field of cosmetics or pharmacy, or as the supports of biologically active substances with the controlled release by means of the change of pH. With regard to the reaction fluently proceeding under physiological conditions and with biocompatible initial materials, the crosslinked products of sulfated polysaccharides can be also considered to be a promising material for cell scaffolds in tissue engineering or regenerative medicine, where they can be preferably used for incorporating the cells and their subsequent cultivation. The method described in this invention can be easily realized in the industry, because it is neither expensive, nor time consuming. This is because of the combination of the two steps into one pot without the need of isolation an intermediate. Another advantage presents the absence of toxic, corrosive, or expensive chemicals in the role of an elimination agent, as well as the absence of an organic solvent, as the reaction proceeds exclusively in water. The reaction times are short; and, moreover, the reaction proceeds at room temperatures. The final products are isolated by precipitation with alcohols or inorganic salt solutions without any harmful effect on the environment. In addition, relatively high degrees of substitution (20-25%) are achieved by the proposed method under substantially milder conditions than in (Buffa R., et al: CZ304512, see Table 1 above).

The sulfated polysaccharides modified by the described method of the invention are suitable as precursors for conjugation or crosslinking reactions with various N-nucleophiles resulting in biocompatible materials suitable for biomedical applications, tissue engineering, and regenerative medicine. More particularly, the derivatives prepared by the method of the invention can be used as supports of biologically active substances with their controlled release with the use of changing the pH value, in the field of cosmetics and pharmacy. The derivatives modified by the method of the invention can be used as biocompatible materials for biomedical applications and formation of scaffolds for tissue engineering, or for regenerative medicine.

EXAMPLES

Figure 1:
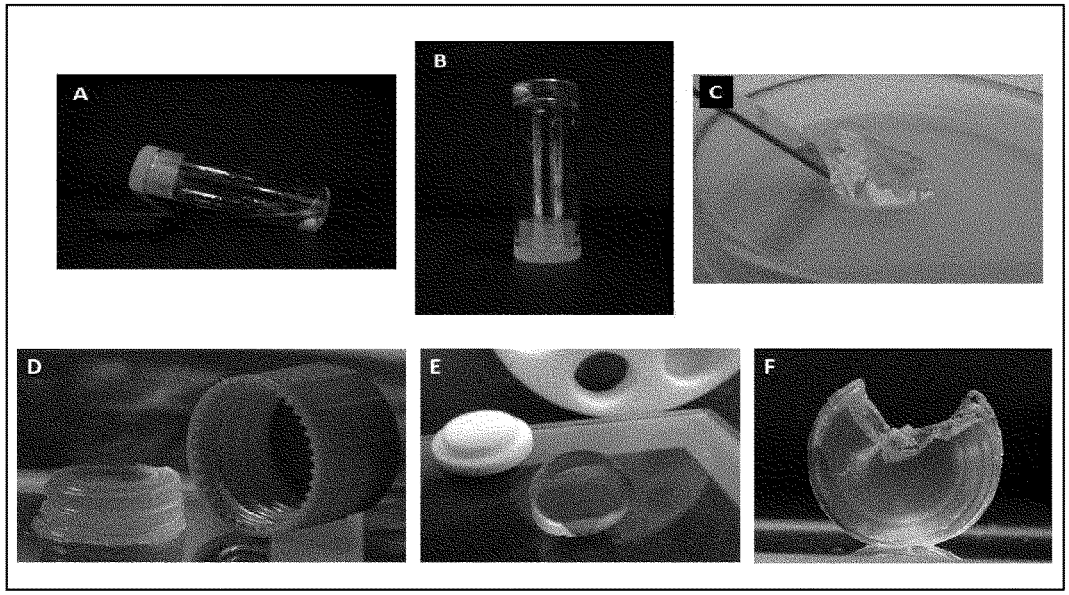
FIG. 1 illustrates the formation of a hydrogel based on oxidized chondroitin sulfate with adipic dihydrazide (Example 21): (a) solution of α,β-unsaturated aldehyde of chondroitin sulfate in PBS, (b) gelation of the solution after the addition of adipic dihydrazide solution in PBS, (c) the hydrogel after 1 h in PBS (pH=7.4, c=0.9% w/v), (d) the use of an illustrative form for the preparation of the hydrogel, (e) the use of a defined form for the preparation of the hydrogel, (f) a detailed view of a segment of the hydrogel.

The term "equivalent" (eq), as used herein, relates to the dimer unit of the sulfated polysaccharide, if not stated otherwise. The percentage is expressed as weight percentage, if not stated otherwise. The molecular weight of the initial chondroitin sulfate (the source: Sigma Aldrich, Ltd., Prague, CZ) is the weight-average molecular weight within the range of $4 \times 10^4$ to $5 \times 10^4$ g·mol$^{-1}$.

The ratio of chondroitin-4-sulfate (type A) and chondroitin-6-sulfate (type C) was 3:2. The material was isolated from an animal material.

The sodium salt of dermatan sulfate (chondroitin sulfate B sodium salt) of the solubility of 5 mg/ml in water was purchased from Sigma Aldrich. The material was isolated from an animal material.

Lambda carrageenan of the solubility of 10 mg/ml in water was purchased from Sigma Aldrich and was isolated from sea algae without gelation properties in the native form.

The degree of substitution of α,β-unsaturated aldehyde in the structure of the sulfated polysaccharide was determined according to the following calculation:

DS=the degree of substitution of α,β-unsaturated aldehyde=100%*(the molar amount of the modified dimer of the sulfated polysaccharide/ (the molar amount of all dimers of the sulfated polysaccharide)

The degree of substitution of the amination reaction in the structure of the sulfated polysaccharide was determined according to the following calculation:

DS=the degree of substitution for amination=100%* (the molar amount of the modified dimer of the sulfated polysaccharide/(the molar amount of all dimers of the sulfated polysaccharide)

FT-IR spectra were measured within the range of 4000-400 cm$^{-1}$ in KBr, by means of the spectrometer Nicolet 6700 FTIR. UV-VIS spectra were measured by means of the apparatus Shimadzu UV-2401PC within the range of 200-600 nm and processed by means of the UV Probe software, version 2.00.

The gelation kinetics was determined by means of the apparatus AR-G2 and TA Analysis was used as the evaluation software. The gel point (Tg) was determined from the time dependence of the elastic and viscous modulus.

The mechanical properties of the selected gels were measured by the compression test by means of the apparatus Instron 3433 and evaluated by means of Bluehill software. The determined parameters for each sample were as follows: Young's modulus for compression, compressive strength, deformation at ultimate strength, and tenacity.

The surface morphology of the lyophilized materials was analysed by means of the electron microscope Zeiss Ultra Plus.

Deacetylated hyaluronic acid was prepared by deacetylation with hydrazine according to Buffa R., et al CZ304512.

Aminopropoxyle and hydrazine derivative of hyaluronic acid were prepared by the reductive amination according to Buffa R., et al.: WO2011069474.

LIST OF ABBREVIATIONS

TEMPO—2,2,6,6-tetramethyl-1-piperidinyloxy radical
4-AcNH-TEMPO—TEMPO with an acetamide group in the 4$^{th}$ position
PBS—phosphate buffered saline
RGD peptide—peptide of the sequence of aminohexane acid-Gly-Arg-Gly-Asp-NH$_2$
AMK—amino acid
IPA—isopropylalcohol
DMSO—dimethylsulfoxide

Example 1

Preparation of α,β-Unsaturated Aldehyde of Chondroitin Sulfate

Method 1: An aqueous solution of sodium hypochlorite (0.8 eq, 11% of active chlorine) was gradually added into a 2% aqueous solution of chondroitin sulfate (200 mg, Mw=4.5×10$^4$ g·mol$^{-1}$) cooled to 5° C., containing disodium phosphate dodecahydrate (2.2 eq), sodium bromide (0.8 eq) and 4-AcNH-TEMPO (0.01%). The mixture was stirred for 2 h at 5° C. Then ethanol (10 eq) was added to the reaction which was stirred for an additional hour at the room temperature.

The product was isolated by precipitation with IPA and analysed by NMR.

DS=23% (determined by NMR), Mw=2.1×10$^4$ g·mol$^{-1}$ (determined by SEC MALLS)

Method 2: An aqueous solution of sodium hypochlorite (0.8 eq, 11% of active chlorine) was gradually added into a 2% aqueous solution of chondroitin sulfate (200 mg, Mw=4.5×10$^4$ g·mol$^{-1}$) cooled to 5° C., containing sodium bromide (0.8 wq) and 4-AcNH-TEMPO (0.01%). The mixture was stirred for 2 h at 5° C. Then ethanol (10 eq) was added to the reaction which was stirred for an additional hour at the room temperature. The product was isolated by precipitation with IPA and analysed by NMR.

DS=20% (determined by NMR)

Spectral analysis of α,β-unsaturated aldehyde of chondroitin sulfate: NMR $^1$H (500 MHz, D$_2$O, δ ppm): 2.02 (3H, Ac—NH—, bs), 4.31 (1H, H2, bs), 4.49 (1H, H3, bs), 5.20 (1H, H1, bs), 6.34 (1H, H4, bs), 9.21 (1H, H6, bs);

NMR $^1$H-$^1$H COSY (D$_2$O), crosspeaks, δ ppm: 4.31-4.49, 4.31-5.20, 4.49-6.34; NMR $^1$H-$^{13}$C HSQC (D$_2$O), crosspeaks, δ ppm: 2.02-25.1, 4.31-51.0, 4.49-73.1, 5.20-98.6, 6.34-122.0, 9.21-189.0;

NMR DOSY (D$_2$O), log D ((2.02, Ac—NH—), (4.31, H2), (4.49, H3), (5.20, H1), (6.34, H4), (9.21; H6))~−10.3 m$^2$ s$^{-1}$, log D (4.72, H$_2$O)~−8.6 m$^2$ s$^{-1}$;

IR (KBr, cm$^{-1}$): 1725, 1650 (ν C=O st), 1615, 1663 (ν C=C st);

UV/Vis (0.1%, H$_2$O); $\lambda_{max1,2}$ (C$_\beta$=C$_\alpha$—C=O)=254 nm (π→π*), 300-350 (π→π*).

Example 2

Preparation of α,β-Unsaturated Aldehyde of Chondroitin Sulfate

An aqueous solution of sodium hypochlorite (0.4 eq, 11% of active chlorine) was gradually added into a 2% aqueous solution of chondroitin sulfate (200 mg, Mw=4.5×10$^4$ g·mol$^{-1}$) cooled to 5° C., containing disodium phosphate dodecahydrate (2.2 eq), sodium bromide (0.4 eq) and 4-AcNH-TEMPO (0.01%). The mixture was stirred for 2 hours at 5° C. Then ethanol (10 eq) was added to the reaction which was stirred for an additional hour at the room temperature. The product was isolated by precipitation with IPA and analysed by NMR.

DS=2% (determined by NMR), Mw=2.8×10$^4$ g·mol$^{-1}$ (determined by SEC MALLS). The structural analysis of the product is presented in Example 1.

Example 3

Preparation of α,β-Unsaturated Aldehyde of Chondroitin Sulfate

An aqueous solution of sodium hypochlorite (1 eq, 11% of active chlorine) was gradually added into a 2% aqueous solution of chondroitin sulfate (200 mg, Mw=4.5×10$^4$ g·mol$^{-1}$) cooled to 5° C., containing disodium phosphate dodecahydrate (2.2 eq), sodium bromide (1 eq) and 4-AcNH-TEMPO (0.01%). The mixture was stirred for 2 hours at 5° C. Then ethanol (10 eq) was added to the reaction which was stirred for an additional hour at the room temperature. The product was isolated by precipitation with IPA and analysed by NMR.

DS=21% (determined by NMR), Mw=2.0×10$^4$ g·mol$^{-1}$ (determined by SEC MALLS). The structural analysis of the product is presented in Example 1.

Example 4

Preparation of α,β-Unsaturated Aldehyde of Chondroitin Sulfate

An aqueous solution of sodium hypochlorite (2 eq, 11% of active chlorine) was gradually added into a 2% aqueous solution of chondroitin sulfate (200 mg, Mw=4.5×10$^4$ g·mol$^{-1}$) cooled to 5° C., containing disodium phosphate dodecahydrate (2.2 eq), sodium bromide (2 eq) and 4-AcNH-TEMPO (0.01%). The mixture was stirred for 2 hours at 5° C. Then ethanol (10 eq) was added to the reaction which was stirred for an additional hour at the room temperature. The product was isolated by precipitation with IPA and analysed by NMR.

DS=21% (determined by NMR), Mw=1.8×10$^4$ g·mol$^{-1}$ (determined by SEC MALLS). The structural analysis of the product is presented in Example 1.

Example 5

Preparation of α,β-Unsaturated Aldehyde of Dermatan Sulfate

An aqueous solution of sodium hypochlorite (0.8 eq, 11% of active chlorine) was gradually added into a 2% aqueous solution of dermatan sulfate (200 mg, 0.42 mol) cooled to 5° C., containing disodium phosphate dodecahydrate (2.2 eq), sodium bromide (0.8 eq) and 4-AcNH-TEMPO (0.01%). The mixture was stirred for 2 hours at 5° C. Then ethanol (10 eq) was added to the reaction which was stirred for an additional hour at the room temperature. The product was isolated by precipitation with IPA and analysed by NMR.

DS=20% (determined by NMR)

Spectral analysis of α,β-unsaturated aldehyde of dermatan sulfate: NMR $^1$H (500 MHz, D$_2$O, δ ppm): 2.01 (3H, Ac—NH—, bs), 6.30 (1H, H4, bs), 9.20 (1H, H6, bs).

Example 6

Preparation of α,β-Unsaturated Aldehyde of Carrageenan

An aqueous solution of sodium hypochlorite (0.8 eq, 11% of active chlorine) was gradually added into a 1% aqueous solution of carrageenan (200 mg, 0.31 mol) cooled to 10° C., containing disodium phosphate dodecahydrate (2.2 eq), sodium bromide (0.8 eq) and 4-AcNH-TEMPO (0.01%). The mixture was stirred for 2 hours at 10° C. Then ethanol (10 eq) was added to the reaction which was stirred for an additional hour at the room temperature. The product was isolated by precipitation with IPA and analysed by NMR.

DS=10% (determined by NMR)

Spectral analysis of α,β-unsaturated aldehyde of carrageenan: NMR $^1$H (500 MHz, D$_2$O, δ ppm): 6.30 (1H, H4, bs), 9.20 (1H, H6, bs).

Example 7

Binding of Hydrazine to α,β-Unsaturated Aldehyde of Chondroitin Sulfate

Hydrazine hydrate (2 eq) was added to a 2% solution of α,β-unsaturated aldehyde of chondroitin sulfate (20 mg, DS=23%, Mw=2.1×10$^4$ g·mol$^{-1}$) in D$_2$O. The reaction was stirred for 24 h at the room temperature. The product was analysed in the form of a crude reaction mixture.

DS=20% (determined by NMR)

NMR $^1$H (500 MHz, D$_2$O, δ ppm): 5.40 (1H, —C̲H̲=C—CH=N—, bs), 7.38 (1H, —CH=C—C̲H̲=N—, bs)

Example 8

Binding of Butylamine to α,β-Unsaturated Aldehyde of Chondroitin Sulfate

Method 1: Butylamine (0.2 eq) was added to a 2% solution of α,β-unsaturated aldehyde of chondroitin sulfate (20 mg, DS=23%, Mw=2.1×10$^4$ g·mol$^{-1}$) in D$_2$O. The reaction was stirred for 24 h at the room temperature and pH=11.20. The product was analysed in the form of a crude reaction mixture.

DS=20% (determined by NMR)

NMR $^1$H (500 MHz, D$_2$O, δ ppm): 5.67 (1H, —C̲H̲=C—CH=N—, bs), 7.74 (1H, —CH=C—C̲H̲=N—, bs)

Method 2: Deuterated acetic acid (14.5 μL) was added to a NMR sample of method 1. The measured pH was 4.10 and the sample was then analysed by NMR.

DS=0% (determined by NMR)

Example 9

Binding of Butylamine to α,β-Unsaturated Aldehyde of Chondroitin Sulfate

Butylamine (0.2 eq) was added to a 2% solution of α,β-unsaturated aldehyde of chondroitin sulfate (20 mg, DS=23%, Mw=2.1×10$^4$ g·mol$^{-1}$) in deuterated PBS. The reaction was stirred for 24 h at the room temperature and pH=7.30. The product was analysed in the form of a crude reaction mixture.

DS=0% (determined by NMR)

Example 10

Binding of Hexane-1,6-Diamine to α,β-Unsaturated Aldehyde of Chondroitin Sulfate Hexane-1,6-diamine (0.5 eq) was added to a 2% solution of α,β-unsaturated aldehyde of chondroitin sulfate (20 mg, DS=23%, Mw=2.1×10$^4$ g·mol$^{-1}$) in D$_2$O. The reaction was stirred for 24 h at the room temperature and pH=11.60. The product was analysed in the form of a crude reaction mixture.

DS=20% (determined by NMR)

NMR $^1$H (500 MHz, D$_2$O, δ ppm): 5.68 (1H, —C<u>H</u>═C—CH═N—, bs), 7.74 (1H, —CH═C—C<u>H</u>═N—, bs)

Example 11

Binding of Propoxyamine to α,β-Unsaturated Aldehyde of Chondroitin Sulfate

Propoxyamine hydrochloride (0.5 eq) was added to a 2% solution of α,β-unsaturated aldehyde of chondroitin sulfate (20 mg, DS=23%, Mw=2.1×10$^4$ g·mol$^{-1}$) in D$_2$O. The reaction was stirred for 24 h at the room temperature and pH=3.90. The product was analysed in the form of a crude reaction mixture.

DS=20% (determined by NMR)

NMR $^1$H (500 MHz, D$_2$O, δ ppm): 5.57 and 6.88 (1H, —C<u>H</u>═C—CH═N—, bs), 7.52 and 7.70 (1H, —CH═C—C<u>H</u>═N—, bs)

Example 12

Binding of Lysine to α,β-Unsaturated Aldehyde of Chondroitin Sulfate

Lysine hydrochloride (0.5 eq) was added to a 2% solution of α,β-unsaturated aldehyde of chondroitin sulfate (20 mg, DS=23%, Mw=2.1×10$^4$ g·mol$^{-1}$) in deuterated PBS. The reaction was stirred for 24 h at the room temperature and pH=7.46. The product was analysed in the form of a crude reaction mixture.

DS=4% (determined by NMR)

NMR $^1$H (500 MHz, D$_2$O, δ ppm): 5.69-5.75 (1H, —C<u>H</u>═C—CH═N—, bs), 7.70-7.75 (1H, —CH═C—C<u>H</u>═N—, bs)

Example 13

Binding of Lysine to α,β-Unsaturated Aldehyde of Chondroitin Sulfate

Lysine hydrochloride (0.5 eq) was added to a 2% solution of α,β-unsaturated aldehyde of chondroitin sulfate (20 mg, DS=23%, Mw=2.1×10$^4$ g·mol$^{-1}$) in D$_2$O. pH of the reaction was adjusted to 8.40 by adding sodium bicarbonate (2 eq). The reaction was stirred for 24 h at the room temperature. The product was analysed in the form of a crude reaction mixture.

DS=7% (determined by NMR)

The structural analysis is presented in Example 12.

Example 14

Binding of RGD Peptide to α,β-Unsaturated Aldehyde of Chondroitin Sulfate

RGD peptide (0.2 eq, sequence Ahx-Gly-Arg-GlyAsp-NH$_2$) was added to 2% solution of α,β-unsaturated aldehyde of chondroitin sulfate (20 mg, DS=23%, Mw=2.1×10$^4$ g·mol$^{-1}$) in D$_2$O. The reaction was stirred for 24 h at the room temperature and pH=4.22. The product was analysed in the form of a crude reaction mixture.

DS=0% (determined by NMR)

Example 15

Binding of RGD Peptide to α,β-Unsaturated Aldehyde of Chondroitin Sulfate

RGD peptide (0.2 eq, sequence Ahx-Gly-Arg-GlyAsp-NH$_2$) was added to a 2% solution of α,β-unsaturated aldehyde of chondroitin sulfate (20 mg, DS=23%, Mw=2.1×10$^4$ g·mol$^{-1}$) in deuterated PBS. The reaction was stirred for 24 h at the room temperature and pH=7.22. The product was analysed in the form of a crude reaction mixture.

DS=4% (determined by NMR)

NMR $^1$H (500 MHz, D$_2$O, δ ppm): 5.68 (1H, —C<u>H</u>═C—CH═N—, bs), 7.74 (1H, —CH═C—C<u>H</u>═N—, bs)

Example 16

Binding of RGD Peptide to α,β-Unsaturated Aldehyde of Chondroitin Sulfate

RGD peptide (0.2 eq, sequence Ahx-Gly-Arg-GlyAsp-NH$_2$) was added to a 2% solution of α,β-unsaturated aldehyde of chondroitin sulfate (20 mg, DS=23%, Mw=2.1×10$^4$ g·mol$^{-1}$) in D$_2$O. pH of the reaction was adjusted to 10.49 by adding sodium bicarbonate (2 eq). The reaction was stirred for 24 h at the room temperature. The product was analysed in the form of a crude reaction mixture.

DS=20% (determined by NMR)

The structural analysis is presented in the Example 15.

Example 17

Binding of Aniline to α,β-Unsaturated Aldehyde of Chondroitin Sulfate

Aniline (0.3 eq) was added to a 2% solution of α,β-unsaturated aldehyde of chondroitin sulfate (20 mg, DS=23%, Mw=2.1×10$^4$ g·mol$^{-1}$) in D$_2$O. pH of the reaction was adjusted to 4.22 by adding deuterated acetic acid (8.8 μL). The reaction was stirred for 24 h at the room temperature. The product was analysed in the form of a crude reaction mixture.

DS=0% (determined by NMR)

Example 18

Binding of Aniline to α,β-Unsaturated Aldehyde of Chondroitin Sulfate

Aniline (0.3 eq) was added to a 2% solution of α,β-unsaturated aldehyde of chondroitin sulfate (20 mg, DS=23%, Mw=2.1×10$^4$ g·mol$^{-1}$) in deuterated PBS. The reaction was stirred for 24 h at the room temperature and pH=7.42. The product was analysed in the form of a crude reaction mixture.

DS=5% (determined by NMR)

NMR $^1$H (500 MHz, D$_2$O, δ ppm): 5.93 (1H, —C<u>H</u>═C—CH═N—, bs), 8.03 (1H, —CH═C—C<u>H</u>═N—, bs)

Example 19

Binding of Aniline to α,β-Unsaturated Aldehyde of Chondroitin Sulfate

Aniline (0.3 eq) was added to a 2% solution of α,β-unsaturated aldehyde of chondroitin sulfate (20 mg, DS=23%, Mw=2.1×10$^4$ g·mol$^{-1}$) in D$_2$O. pH of the reaction was adjusted to 10.73 by adding sodium carbonate. The reaction was stirred for 24 h at the room temperature. The product was analysed in the form of a crude reaction mixture.

DS=25% (determined by NMR)

The structural analysis is presented in the Example 18.

Example 20

Binding of Dihydrazide Adipate to α,β-Unsaturated Aldehyde of Chondroitin Sulfate Dihydrazide adipate (3 eq) was added to a 2% solution of α,β-unsaturated aldehyde of chondroitin sulfate (20 mg, DS=23%, Mw=2.1×10$^4$ g·mol$^{-1}$) in D$_2$O. The reaction was stirred for 24 h at the room temperature and pH=7.50. The product was analysed in the form of a crude reaction mixture.

DS=20% (determined by NMR)

NMR $^1$H (500 MHz, D$_2$O, δ ppm): 1.64 (4H, DHA$_{2,3}$, bs), 2.04 (3H, Ac—NH—, bs), 2.34 (4H, DHA$_{1,4}$, bs), 4.28 (1H, H2, bs), 4.36 (1H, H3, bs), 5.20 (1H, H1, bs), 5.62 (1H, H4 cis, bs), 5.68 (1H, H4 trans, bs), 7.52-7.48 (1H, H6 cis, bs), 7.61 (1H, H6 trans, bs);

NMR $^1$H-$^1$H COSY (D$_2$O), crosspeaks, δ ppm: 1.64-2.34, 4.28-5.20, 4.36-5.68; NMR $^1$H-$^{13}$C HSQC (D$_2$O), crosspeaks, δ ppm: 1.64-24.9, 2.34-34.1, 4.28-51.0, 4.36-73.6, 5.20-98.8, 5.68-111.3, 7,61148.5;

NMR DOSY (D$_2$O), log D ((2.04, Ac—NH—), (4.28, H2), (4.36, H3), (5.20, H1), (5.62 and 5.68, H4 cis/trans), (7.52 and 7.68, H6 cis/trans))~−10.4 m$^2$ s$^{-1}$, log D (4.72, H$_2$O)~−8.6 m$^2$ s$^{-1}$;

IR (KBr, cm$^{-1}$): 1640-1650 (ν—C=N-st);

UV/Vis (0.1%, H$_2$O); λ$_{max1,2}$ (—C=N—)=280 nm (π→π*).

Example 21

Figure 2:
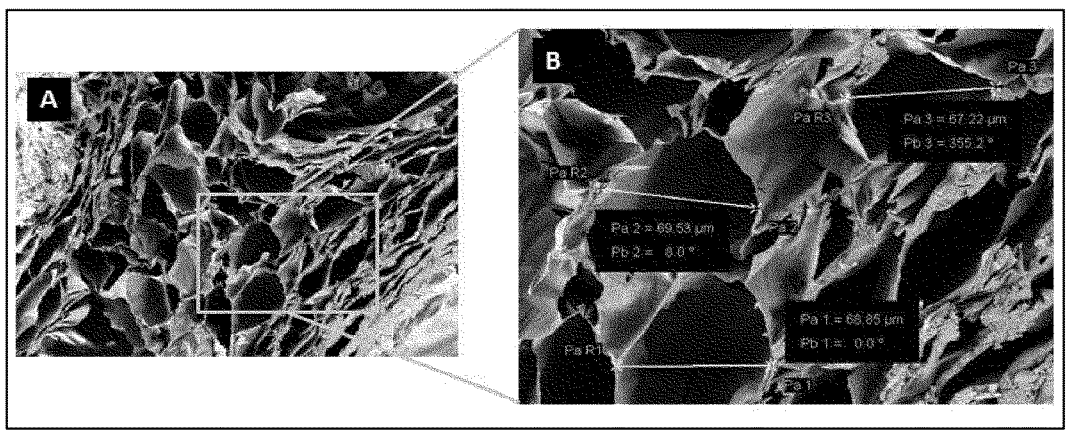
FIG. 2 Photographs of the lyophilized hydrogel based on the oxidized chondroitin sulfate with adipic dihydrazide taken by the scanning electron microscope: (a) a cross section, magnification 200×, detection of secondary electrons, (b) an enlarged section of the porous structure of the hydrogel with the measured diameter.

Crosslinking of α,β-Unsaturated Aldehyde of Chondroitin Sulfate with Dihydrazide Adipate Dihydrazide adipate (0.12 eq, binding sites ratio 1:1) in PBS was added to an 8% solution of α,β-unsaturated aldehyde of chondroitin sulfate (40 mg, DS=23%, Mw=2.1×10$^4$ g·mol$^{-1}$) in PBS (pH=7.40, c=0.9% w/v). After the addition of the solution of dihydrazide adipate, the gelation occurred in time (Tg=34 s). The elastic gel was photographed (FIG. 1), lyophilized, and analyzed by SEM (FIG. 2).

Young's modulus of elasticity in compression=9×10$^3$ Pa
Ultimate strength in compression=64×10$^3$ Pa
Deformation at ultimate strength=64%
Tenacity=3668 J·m$^{-3}$

Example 22

Crosslinking of α,β-Unsaturated Aldehyde of Dermatan Sulfate with Dihydrazide Adipate Dihydrazide adipate (0.1 eq, binding sites ratio 1:1) in PBS was added to an 8% solution of α,β-unsaturated aldehyde of dermatan sulfate (40 mg, DS=20%, Mw≤40 kDa) in PBS (pH=7.40, c=0.9% w/v). After the addition of the solution of dihydrazide adipate, the gelation proceeded.

Example 23

Crosslinking of α,β-Unsaturated Aldehyde of Carrageenan with Dihydrazide Adipate 40 μL of dihydrazide adipate (0.05 eq) in PBS was added to an 8% solution of α,β-unsaturated aldehyde of carrageenan (40 mg, DS=10%, Mw≤50 kDa) in PBS (pH=7.40, c=0.9% w/v). After the addition of the solution of dihydrazide adipate, the viscosity increased.

Example 24

Crosslinking of α,β-Unsaturated Aldehyde of Chondroitin Sulfate with Hydrazide Derivative of Hyaluronic Acid A 4% solution of hydrazide derivative of hyaluronic acid (9.2 mg, DS=25%, Mw=138×10$^3$ g·mol$^{-1}$) in PBS (pH=7.4, c=0.9% w/v) was added to a 4% solution of α,β-unsaturated aldehyde of chondroitin sulfate (10 mg, DS=23%, Mw=2.1×10$^4$ g·mol$^{-1}$) in PBS. After mixing the solutions, the gelation occurred in time (Tg=109 s).

Young's modulus of elasticity in compression=6×10$^3$ Pa
Ultimate strength in compression=840×10$^3$ Pa
Deformation at ultimate strength=96%
Tenacity=11978 J·m$^{-3}$

Example 25

Crosslinking of α,β-Unsaturated Aldehyde of Chondroitin Sulfate with Deacetylated Hyaluronic Acid A 2% solution of deacetylated hyaluronic acid (2 eq, DS=11%, Mw=116 kDa, binding sites ratio 1:1) in PBS (pH=7.4, c=0.9% w/v) was added to a 4% solution of α,β-unsaturated aldehyde of chondroitin sulfate (10 mg, DS=23%, Mw=2.1×10$^4$ g·mol$^{-1}$) in PBS (pH=7.40, c=0.9% w/v). The reaction mixture was stirred at the room temperature, wherein an increase in viscosity was observed after 0.5 h, and an elastic gel was formed after 1 h.

Young's modulus of elasticity in compression=3×10$^3$ Pa
Ultimate strength in compression=395×10$^3$ Pa
Deformation at ultimate strength=95%
Tenacity=14670 J·m$^{-3}$

Example 26

Preparation of the Acid Form of Chondroitin Sulfate

A 1% solution of chondroitin sulfate (500 mg, 1.1 mmol) in distilled water was prepared. The solution was cooled to 5° C. and 1.2 ml of Amberlite IR 120 Na(H$^+$) catex was added. The reaction mixture was stirred for 24 h at 5° C. The catex was filtered off, the product was frozen and lyophilized. Its solubility in DSMO was tested and found satisfactory.

Example 27

Preparation of Deacetylated Chondroitin Sulfate

A 1% solution of acid form of chondroitin sulfate was prepared (200 mg, 0.44 mmol, Mw≤40 kDa) in DMSO. The solution was degassed by a stream of nitrogen. 10.6 mL of hydrazine hydrate and 3 eqs of hydrazine sulfate were added. The reaction mixture was stirred for 24 h at 60° C. under nitrogen. Then NaHCO$_3$ was added to the reaction mixture. The product was isolated by precipitation with IPA.

DS=10% (determined by NMR), Mw=1.8×10$^4$ g·mol$^{-1}$ (determined by SECMALLS)

NMR $^1$H (500 MHz, 1% NaOD v D$_2$O, δ ppm): 3.01 (1H, —CH—C—CH=N—, bs) HSQC (500 MHz, D$_2$O, δ ppm): crosspeak: 3.42-52.2 ppm

Example 28

Crosslinking of α,β-Unsaturated Aldehyde of Chondroitin Sulfate with Deacetylated Chondroitin Sulfate An 8% solution of deacetylated chondroitin sulfate (2 eq, DS=10%, Mw=1.8×10$^4$ g·mol$^{-1}$, binding sites ratio=1/0.85) in PBS (pH=7.4, c=0.9% w/v) was added to an 8% solution of α,β-unsaturated aldehyde of chondroitin sulfate (20 mg, DS=23%, Mw=2.1×10$^4$ g·mol$^{-1}$) in PBS (pH=7.40, c=0.9% w/v). The reaction mixture was stirred at the room temperature, wherein an increase in viscosity was observed after 0.5 h, and an elastic gel was formed after 3 h.

Young's modulus of elasticity in compression=3×10³ Pa

Ultimate strength in compression=774×10³ Pa

Deformation at ultimate strength=95%

Tenacity=16489 J·m⁻³

Example 29

Crosslinking of α,β-Unsaturated Aldehyde of Chondroitin Sulfate with Propoxyamine A PBS solution of propoxyamine hydrochloride (0.12 eq, binding sites ratio=1/1) was added to a 10% solution of α,β-unsaturated aldehyde of chondroitin sulfate (50 mg, DS=23%, Mw=2.1×10⁴ g·mol⁻¹) in PBS (pH=7.40, c=0.9% w/v), wherein a gel was formed in time (Tg=110 s).

Young's modulus of elasticity in compression=8×10³ Pa

Ultimate strength in compression=74×10³ Pa

Deformation at ultimate strength=65%

Tenacity=3768 J·m⁻³

Example 30

Figure 4:
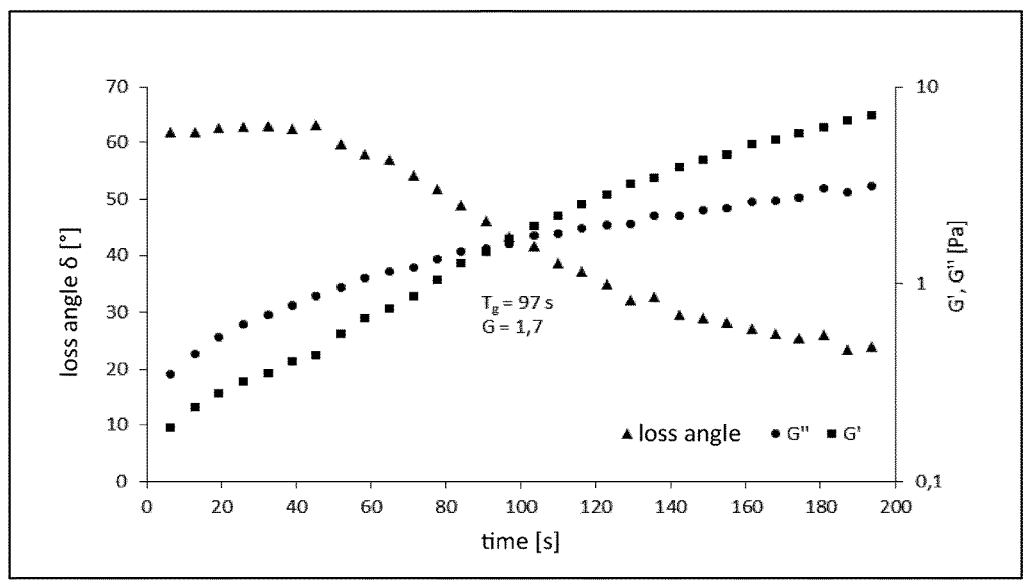
FIG. 4 Kinetics of the gelation in Example 30, with the determination of the gel point (Tg 97 s, T=45° C.). A graphical representation of the dependence of elastic (G') and viscous (G") modulus in time.

Measurement of Gelation Kinetics of Crosslinking Reaction of α,β-Unsaturated Aldehyde of Chondroitin Sulfate with Aminopropoxyl Derivative of Hyaluronic Acid The measurement of gelation kinetics was performed by means of a 4% sample of α,β-unsaturated aldehyde of chondroitin sulfate (10 mg, DS=23%, Mw=2.1×10⁴ g·mol⁻¹) in PBS (pH=7.40, c=0.9% w/v) with a 4% solution of aminopropoxyl derivative of hyaluronic acid (1 eq, DS=25%, Mw=66 kDa) in PBS (pH=7.4, c=0.9% w/v). The gelation time, i.e. the stage, when the first macroscopic gel network was formed, was determined to be (Tg=97 s, FIG. 4).

Example 31

Comparison of Mechanical Properties of Hydrogels Based on the Crosslinked α,β-Unsaturated Aldehyde of Chondroitin Sulfate and α,β-Unsaturated Aldehyde of Hyaluronan Solution 1: 4% solution of α,β-unsaturated aldehyde of chondroitin sulfate (DS=23%, Mw=2.1×10⁴ g·mol⁻¹, Example 1) in PBS (pH=7.40, c=0.9% w/v).

Solution 2: 4% solution of α,β-unsaturated aldehyde of hyaluronic acid (DS=7%, Mw=2.5×10⁴ g·mol⁻¹) in PBS (pH=7.40, c=0.9% w/v).

Solution 3: 4% solution of aminopropoxyl derivative of hyaluronic acid (DS=25%, Mw=66 kDa) in PBS (pH=7.40, c=0.9% w/v).

Hydrogels were prepared from the said solutions by mixing their equivalent volume ratios in the following combinations: solution 1+solution 3 (sample A) and solution 2+solution 3 (sample B). Samples A and B were left to mature at the room temperature for 3 hours. Then the mechanical properties of the materials were measured, namely Young's modulus of elasticity in compression, ultimate strength in compression, and deformation at ultimate strength (Table 2).

TABLE 2

Comparison of the mechanical properties of the hydrogels based on crosslinked α,β-unsaturated aldehydes derived from chondroitin sulfate and hyaluronic acid

| Sample | Young's modulus of elasticity in compression (kPa) | ultimate strength in compression (kPa) | Elongation in ultimate strength (%) |
|---|---|---|---|
| A | 11 | 30 | 52 |
| B | 7 | 58 | 76 |

The measured data indicate the advantages of the use of the material of a higher degree of substitution in the chondroitin sulfate derivative (sample A), because the hydrogels prepared from this derivative have a higher rigidity and show a lower deformation rate in comparison with the hyaluronic acid derivative (sample B). As the samples were of the same molecular weight and were analysed under the same conditions, this fact seems to be the consequence of a higher crosslink density and it directly correlates, while maintaining the same molecular weight, with the higher degree of substitution of the α,β-unsaturated aldehyde in the structure of the modified polysaccharide.

Example 32

Figure 3:
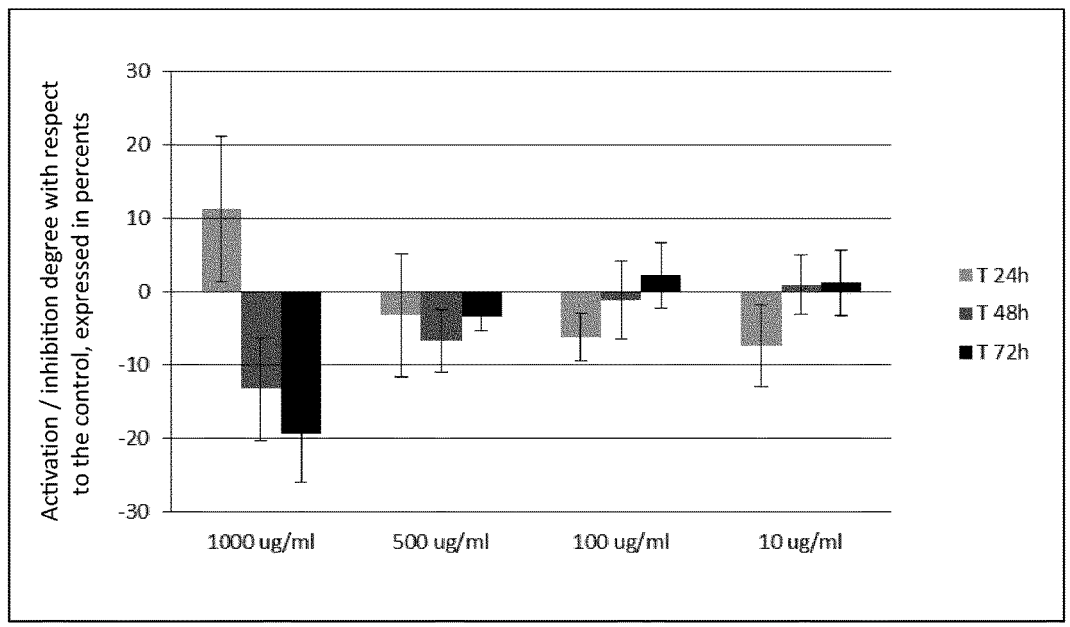
FIG. 3 illustrates the results of the cell viability tests of 3T3 fibroblasts in α,β-unsaturated aldehyde of chondroitin sulfate (Mw=4×10⁴ g/mol, DS=20%). The activation vs inhibition curve, expressed in %, with respect to the control in time T=0 h (100%). Evaluation by means of MTT method, six repetitions.

Viability Tests of 3T3 Fibroblasts in the Presence of α,β-Unsaturated Aldehyde of Chondroitin Sulfate The tested substance, α,β-unsaturated aldehyde of chondroitin sulfate (DS=20%, Mw=40 kDa), was dissolved in a complete 3T3 medium. The solution was filtered via a 0.22 μm filter. The final test concentrations of the tested solution were 10, 100, 500, and 1000 μg·mL⁻¹. 3T3 cells of the density of 3000 cells per a well were inoculated into 96-well plates. Before the treatment, the cells were cultured for 24 hours in a complete medium. The cell viability was evaluated by spectrophotometry by means of 3-[4,5-dimethylthiazole-2-yl]-2,5-diphenyl tetrazolium bromide (MTT method) in the intervals of 0, 24, 48, 72 hours. The whole experiment was supplemented with a set of non-treated controls and blank samples. The measured optical density data were converted into percentage formulation related to the control in the time T0 hours (the ratio of the optical density of the treated sample with respect to the optical density of the non-treated control T0, multiplied by 100) and the standard error of the mean (SEM) was calculated. The results of the test are graphically presented at FIG. 3.

The invention claimed is:

1. A derivative of a sulfated polysaccharide having as a part of its polymer chain at least one galactopyranose ring modified according to the general formula I or II, said ring containing a double bond in the 4$^{th}$ and 5$^{th}$ position in a conjugation with an aldehyde in the 6$^{th}$ position according to the general formula I or next to its hydrated form according to the general formula II

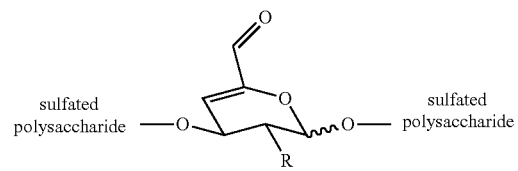

(I)

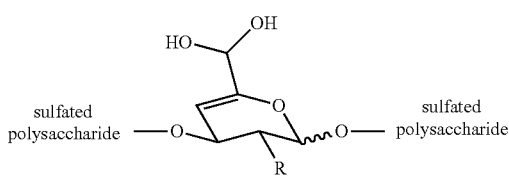

where
R is OH, O—SO$_2$—OH, O—SO$_2$—ONa or NH—Ac.

2. The derivative of a sulfated polysaccharide according to claim 1, characterized in that the polysaccharide is selected from the group comprising chondroitin sulfate, dermatan sulfate, carrageenan, and their pharmaceutically acceptable derivatives and/or salts.

3. The derivative of a sulfated polysaccharide according to claim 1, characterized in that the polysaccharide has the molecular weight within the range of $1 \times 10^3$ to $5 \times 10^4$ g·mol$^{-1}$ and that the degree of modification of the polysaccharide to an alfa, beta-unsaturated aldehyde is within the range of 1 to 40%.

4. A method of preparation of the derivatives of sulfated polysaccharides as defined in claim 1, characterized in that the sulfated polysaccharide, that is soluble in water in its native form and that contains at least one galactopyranose unit sulfated in the $4^{th}$ position which is bound via $\alpha(1\rightarrow3)$ or $\beta(1\rightarrow3)$ O-glycosidic bond in the polymer chain, according to the general structural formula (III)

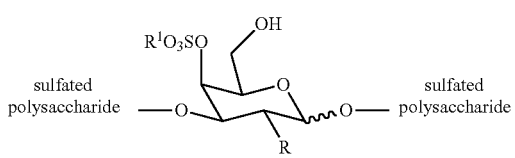

where
R is OH, O—SO$_2$—OH, O—SO$_2$—ONa or NH—C(O)CH$_3$, R$^1$ is H or Na, is oxidized to an aldehyde in the $6^{th}$ position by means of the system 4-N-acetyl-TEMPO/NaClO in water or in an aqueous solution of inorganic salts, at 5 to 25° C., and immediately after the oxidation the reaction mixture is subjected to elimination in the same reaction mixture to form the derivative of the sulfated polysaccharide defined in claim 1.

5. The method of preparation according to claim 4, characterized in that a sulfated polysaccharide of the molecular weight within the range of $1 \times 10^4$ to $5 \times 10^6$ g·mol$^{-1}$ is used.

6. The method of preparation according to claim 4, characterized in that a sulfated polysaccharide selected from the group comprising chondroitin sulfate, dermatan sulfate, carrageenan, and their pharmaceutically acceptable derivatives and/or salts is used.

7. The method of preparation according to claim 4, characterized in that the molar amount of 4-N-acetyl-TEMPO is 0.01 to 0.2 equivalent and the molar amount of NaClO is within the range of 0.1 to 2.0 equivalents with respect to a dimer of the sulfated polysaccharide.

8. The method of preparation according to claim 4, characterized in that the aqueous solution of inorganic salts is an aqueous solution containing an alkaline metal salt and/or a buffer.

9. The method of preparation according to claim 4, characterized in that the elimination proceeds at 5 to 25° C., and without the isolation of the saturated C6-aldehyde in the galactopyranose subunit sulfated in the $4^{th}$ position.

10. A method of modification of the derivative defined in claim 1, characterized in that the derivative is reacted with an amine according to the general formula R$^2$—NH$_2$, where R$^2$ is an alkyl, aryl, hetaryl, linear, or branched C$_1$ to C$_{30}$ chain, optionally containing N, S, or O atoms.

11. The method of modification according to claim 10, characterized in that the amine is an amino acid or a peptide.

12. The method of modification of the derivative according to claim 10, characterized in that the derivative reacts with an amine which is a biologically acceptable polymer with a free amino group.

13. The method of modification according to claim 12, characterized in that the amino group is a direct part of the polymer selected from the group comprising gelatine, chitosan, deacetylated hyaluronic acid, and deacetylated chondroitin sulfate.

14. The method of modification according to claim 12, characterized in that the amino group is bound to the polymer via a linker containing an amino, hydrazine, hydrazide, aminoalkoxy, hydroxyl, carboxyl, thiol group, or any combination thereof.

15. The method of modification according to claim 10, characterized in that the amount of the amine is within the range of 0.05 to 3.0 equivalents with respect to a dimer of the sulfated polysaccharide.

16. The method of modification according to claim 10, characterized in that the reaction with the amine proceeds in water, phosphate buffer, or water-organic solvent system, at the temperature within the range of 20 to 60° C., for 10 min to 150 h.

17. The method of modification according to claim 16, characterized in that the organic solvent is selected from the group comprising water miscible alcohols, in particular isopropanol or ethanol, and water miscible polar aprotic solvents, in particular dimethyl sulfoxide, wherein the water content in the mixture is at least 50% vol.

18. The method of modification of the derivative according to claim 1, characterized in that the derivative is reacted with a water soluble biocompatible bi- and polyfunctional N-nucleophile selected from the group comprising alkyl amines, aryl amines, heteroalkyl amines, hetaryl amines, amino acids, peptides, polymers with a free amino group, hydrazines, hydroxylamines, hydrazides, semicarbazides, or thiosemicarbazides, wherein crosslinking of the derivative occurs.

19. The method of modification according to claim 18, characterized in that the N-nucleophile is hydrazide, deacetylated polysaccharide, or alkoxyamine, and in that the reaction proceeds in phosphate buffer.

* * * * *